US010786395B1

(12) United States Patent
Temkin et al.

(10) Patent No.: US 10,786,395 B1
(45) Date of Patent: Sep. 29, 2020

(54) APPARATUS FOR PROCESSING HEALTHCARE DATA AND STORING AND TRANSMITTING LARGE AMOUNTS OF DATA VIA A BANDAGE OR STICKER

(71) Applicant: Pleiotek, Bethesda, MD (US)

(72) Inventors: Joshua Michael Temkin, Bethesda, MD (US); Brian Richard Teeter, Land O Lakes, FL (US); Melissa Greenfield Temkin, Bethesda, MD (US)

(73) Assignee: Pleiotek, Bethesda, MD (US)

( * ) Notice: Subject to any disclaimer, the term of this patent is extended or adjusted under 35 U.S.C. 154(b) by 0 days.

(21) Appl. No.: 16/882,837

(22) Filed: May 26, 2020

Related U.S. Application Data

(60) Provisional application No. 62/978,353, filed on Feb. 19, 2020, provisional application No. 62/978,350, filed on Feb. 19, 2020.

(51) Int. Cl.
*H04W 4/38* (2018.01)
*H04W 4/80* (2018.01)
*A61F 13/00* (2006.01)
*A61F 13/02* (2006.01)
*A61B 5/00* (2006.01)

(52) U.S. Cl.
CPC ...... *A61F 13/00051* (2013.01); *A61B 5/0022* (2013.01); *A61B 5/6833* (2013.01); *A61F 13/02* (2013.01); *H04W 4/38* (2018.02); *H04W 4/80* (2018.02); *A61F 2013/00944* (2013.01)

(58) Field of Classification Search
CPC ..... H04W 4/38; H04W 4/80; A61F 13/00051; A61F 13/02; A61F 2013/00944; A61F 2013/00953; A61B 5/0022; A61B 5/6833
See application file for complete search history.

(56) References Cited

U.S. PATENT DOCUMENTS 8,861,733 B2 * 10/2014 Benteo .................. G06Q 20/32 380/270
9,455,768 B2 * 9/2016 Griffin ................ H04B 5/0031
2006/0252372 A1 * 11/2006 Liu .................... H04M 1/7253 455/41.2
2009/0033469 A1 * 2/2009 Seppa ................... G01D 9/005 340/10.3
2011/0140703 A1 * 6/2011 Chiao .................. C23C 28/345 324/438
2011/0237230 A1 * 9/2011 Li .......................... H04M 3/54 455/414.1

(Continued)

OTHER PUBLICATIONS

Restriction Requirement, dated Jul. 16, 2020, from corresponding U.S. Appl. No. 16/882,836.

*Primary Examiner* — Dominic E Rego
(74) *Attorney, Agent, or Firm* — Brient IP Law, LLC

(57) ABSTRACT

A smart bandage that serves as a functional bandage includes electronic components that allow the bandage to store large amounts of data. The components can include a processor, battery, data storage media, NFC components, Bluetooth components, and Wi-Fi components. The bandage can remain powered down until receiving an NFC signal, which then causes the bandage to power up its components and communicate using other wireless communications means. Healthcare data compression methods may be used to improve the information storage capabilities of the smart bandage.

18 Claims, 6 Drawing Sheets

100
110
120
130
One or More Databases 150
One or More Healthcare Data Servers 160
One or More Networks 140
One or More Government Agency Data Servers 170
One or More Other Devices 180

(56) References Cited

U.S. PATENT DOCUMENTS

2011/0250843 A1* 10/2011 Heo .................... H04M 1/6066
455/41.2
2013/0053659 A1* 2/2013 Melchert .............. A61B 5/0408
600/309
2014/0350882 A1* 11/2014 Everett ................ A61B 5/6833
702/98
2015/0297437 A1* 10/2015 Neuenhahn .......... A61B 5/4848
601/148
2016/0156603 A1* 6/2016 Janik ................... H04L 63/0853
726/7
2016/0353270 A1* 12/2016 Brisebois ............. H04B 5/0031
2017/0265800 A1* 9/2017 Auchinleck .......... A61B 5/6828
2017/0288736 A1* 10/2017 Zhou .................... H01Q 1/2225
2017/0321629 A1* 11/2017 Boczek ..................... F02F 3/10
2017/0347940 A1* 12/2017 Carr ....................... A61B 5/145
2017/0348156 A1* 12/2017 Duesterhoft ......... A61B 5/6831
2018/0117447 A1* 5/2018 Tran ....................... A42B 3/046
2019/0087554 A1* 3/2019 Fish ..................... H04B 1/3888
2019/0114619 A1* 4/2019 Wilson ............... G06Q 20/3563
2019/0147452 A1* 5/2019 Leung .................. G06Q 20/385
705/41
2019/0183426 A1* 6/2019 Paquet ................. A61B 5/0006
2019/0209022 A1* 7/2019 Sobol .................... A61B 5/1112
2019/0230207 A1* 7/2019 Cheng ..................... H04W 4/80
2019/0328327 A1* 10/2019 Kim ...................... G01J 1/0228
2019/0349652 A1* 11/2019 Greenewald ......... A61B 5/6833
2020/0121245 A1* 4/2020 Barclay .................. A61B 5/445
2020/0188161 A1* 6/2020 Seres .................... A61F 5/4407

* cited by examiner

100
One or More Databases 150
One or More Healthcare Data Servers 160
One or More Government Agency Data Servers 170
One or More Other Devices 180
One or More Networks 140
130
110
120

APPARATUS FOR PROCESSING HEALTHCARE DATA AND STORING AND TRANSMITTING LARGE AMOUNTS OF DATA VIA A BANDAGE OR STICKER

CROSS-REFERENCE TO RELATED APPLICATIONS

This application claims priority to U.S. Provisional Patent Application Ser. No. 62/978,350, filed Feb. 19, 2020, entitled "SYSTEMS AND METHODS FOR STRUCTURED AND CONFIGURABLE DATA COMPRESSION," and to U.S. Provisional Patent Application Ser. No. 62/978,353, filed Feb. 19, 2020, entitled "APPARATUS FOR STORING AND TRANSMITTING LARGE AMOUNTS OF DATA VIA A BANDAGE OR STICKER," each of which is hereby incorporated herein by reference in its entirety.

BACKGROUND

In modern medical settings, the collection, storage, and processing of health data is commonplace, resulting in the accumulation and processing of large amounts of data for each patient and procedure occurring in a typical medical facility. There are environments and operating conditions where patients may have urgent medical needs, but the access to, and ability to process, health data associated with such patients is limited. Such environments and operating conditions are known as "disconnection, intermittent, or low-bandwidth" (DIL) environments or conditions and include any situation where there are limits on the size and/or amount of data that can be transmitted, received, processed, and/or stored at any given time. However, in such environments, the need to collect, store, and exchange information remains. Examples of such environments include battlefields, remote operations, temporary emergency medical facilities, remote military operations, medical operations in times of natural disaster, etc.

SUMMARY

A computer-implemented data processing method for encoding healthcare data, according to various embodiments, may include: receiving, by one or more computer processors, healthcare data comprising a plurality of pieces of healthcare data; determining, by one or more computer processors, a value of a first piece of healthcare data of the plurality of pieces of healthcare data; determining, by one or more computer processors, one or more attributes of the first piece of healthcare data; determining, by one or more computer processors using a look-up table, a byte position for the first piece of healthcare data based on the one or more attributes of the first piece of healthcare data; determining, by one or more computer processors using the look-up table, an encoding type for the first piece of healthcare data based on the one or more attributes of the first piece of healthcare data; generating, by one or more computer processors based on the encoding type for the first piece of healthcare data, an encoded byte representing the first piece of healthcare data; inserting, by one or more processors, the encoded byte representing the first piece of healthcare data into a sequence of encoded bytes at the byte position for the first piece of healthcare data; generating, by one or more computer processors, a data stream comprising the sequence of encoded bytes; and transmitting, by one or more computer processors using one or more wireless communications components, the data stream to a recipient device.

In particular embodiments, the method may include inserting a special byte code into the sequence of encoded bytes, wherein the special byte code indicates one of: (a) a separation of complete medical data records; (b) a separation of medical values; (c) a separation of types of medical data; (d) an end of a complete medical data record; (e) an end of a structure of a medical data record; and (f) an end of a substructure of a medical data record. In particular embodiments, one or more of the plurality of pieces of healthcare data is a piece of healthcare data selected from a group consisting of: (a) a vital sign code; (b) a unit of measurement; (c) an observed measurement; and (d) a timestamp. In particular embodiments, the look-up table comprises a plurality of encoding bytes, and for each encoding byte of the plurality of encoding bytes, the look-up table comprises a respective code system, a respective code value, and a respective display text. In particular embodiments, the look-up table is one of a plurality of look-up tables, and each look-up table of the plurality of look-up tables is associated with a distinct medical domain. In particular embodiments, that method may also include determining that there are no remaining pieces of healthcare data of the plurality of pieces of healthcare data to encode; and at least partially in response to determining that there are no remaining pieces of healthcare data of the plurality of pieces of healthcare data to encode, inserting a special encoded byte into the sequence of encoded bytes at a position in the sequence of encoded bytes immediately following a position of a last encoded byte in the sequence of encoded bytes, wherein the special encoded byte indicates the end of the sequence of encoded bytes. In particular embodiments, the method may also include determining that there is unused space in an amount of data space allotted to the sequence of encoded bytes; and the special encoded byte into the sequence of encoded bytes at a position in the sequence of encoded bytes immediately following a position of a last encoded byte in the sequence of encoded bytes is further inserted into the sequence of encoded bytes at least partially in response to determining that there is unused space in the amount of data space allotted to the sequence of encoded bytes. In particular embodiments, determining the encoding type for the first piece of healthcare data based on the one or more attributes of the first piece of healthcare data comprises determining that the encoding type for the first piece of healthcare data is binary encoding. In particular embodiments, the first piece of healthcare data comprises a character string representation of a numeric value; and generating the encoded byte representing the first piece of healthcare data based on the encoding type for the first piece of healthcare data comprises: converting the character string representation of the numeric value to a binary representation of the numeric value; and generating the encoded byte comprising the binary representation of the numeric value.

A data processing system for encoding healthcare data, according to various embodiments, may include: data reception means for receiving healthcare data comprising a plurality of pieces of healthcare data; healthcare data value determination means for determining a value of a first piece of healthcare data of the plurality of pieces of healthcare data; healthcare data attribute determination means for determining one or more attributes of the first piece of healthcare data; healthcare data encoded byte position determination means for determining a byte position for the first piece of healthcare data based on the one or more attributes of the first piece of healthcare data using a look-up table;

healthcare data encoding type determination means for determining an encoding type for the first piece of healthcare data based on the one or more attributes of the first piece of healthcare data using a look-up table; healthcare data encoded byte generation means for generating an encoded byte representing the first piece of healthcare data based on the encoding type for the first piece of healthcare data; encoded byte insertion means for inserting the encoded byte representing the first piece of healthcare data into a sequence of encoded bytes at the byte position for the first piece of healthcare data; data stream generation means for generating a data stream comprising the sequence of encoded bytes; and wireless transmission means for wirelessly transmitting the data stream to a recipient device.

A data processing system for decoding encoded healthcare data, according to various embodiments, may include: one or more processors; one or more wireless communications components; and computer memory storing computer-executable instructions that, when executed by the one or more processors, cause the one or more processors to perform operations comprising: receiving, at the one or more processors via the one or more wireless communications components, a data stream comprising a sequence of encoded bytes; determining a first byte position within the sequence of encoded bytes of a first encoded byte of the sequence of encoded bytes; determining, based on the first byte position within the sequence of encoded bytes of the first encoded byte, using a look-up table, one or more healthcare data attributes associated with a first piece of healthcare data; determining, based on the one or more healthcare data attributes associated with the first piece of healthcare data, a decoding type for the first piece of healthcare data; generating, based on the decoding type for the first piece of healthcare data, a value of the first piece of healthcare data using the first encoded byte; storing, in the computer memory, the one or more healthcare data attributes associated with the first piece of healthcare data and the value of the first piece of healthcare data; associating, in the computer memory, the one or more healthcare data attributes associated with the first piece of healthcare data and the value of the first piece of healthcare data; and generating a healthcare record comprising the one or more healthcare data attributes associated with the first piece of healthcare data and the value of the first piece of healthcare data.

In particular embodiments, determining the decoding type for the first piece of healthcare data comprises determining that the decoding type for the first piece of healthcare data is binary encoding. In particular embodiments, the first encoded byte comprises a binary representation of a numeric value; and generating, based on the decoding type for the first piece of healthcare data, the value of the first piece of healthcare data using the first encoded byte comprises converting the binary representation of the numeric value to a character string representation of the numeric value. In particular embodiments, one or more of the one or more healthcare data attributes associated with the first piece of healthcare data comprise one or more attributes selected from a group consisting of: (a) a code system; (b) a code value; and (c) a display text. In particular embodiments, one or more healthcare data attributes associated with the first piece of healthcare data comprises a code system, and wherein the code system is the Logical Observation Identifiers Names and Codes (LOINC) system health measurement terminology system. In particular embodiments, the operations may include: determining a second byte position within the sequence of encoded bytes of a second encoded byte of the sequence of encoded bytes; determining, based on the second byte position within the sequence of encoded bytes of the second encoded byte, using the look-up table, that the second encoded byte is a special byte code. In particular embodiments, the special byte code indicates the termination of the data stream.

A non-transitory computer-readable medium, according to various embodiments, may include computer executable instructions for: receiving, by one or more computer processors, healthcare data comprising a plurality of pieces of healthcare data; determining, by one or more computer processors, a first piece of healthcare data of the plurality of pieces of healthcare data; determining, by one or more computer processors, one or more attributes of the first piece of healthcare data; determining, by one or more computer processors, using a look-up table and based on the one or more attributes of the first piece of healthcare data, a byte position for the first piece of healthcare data; determining, by one or more computer processors, using the look-up table and based on the one or more attributes of the first piece of healthcare data, an encoding type for the first piece of healthcare data, wherein the encoding type comprises binary encoding; determining, by one or more computer processors, a numeric value associated with the first piece of healthcare data, wherein the numeric value is representing in the first piece of healthcare data by a character string; determining, by one or more computer processors based on the encoding type for the first piece of healthcare data, a binary representation of the numeric value associated with the first piece of healthcare data; generating, by one or more computer processors, an encoded byte representing the first piece of healthcare data comprising the numeric value associated with the first piece of healthcare data; inserting, by one or more processors, the encoded byte representing the first piece of healthcare data into a sequence of encoded bytes at the byte position for the first piece of healthcare data; generating, by one or more computer processors, a data stream comprising the sequence of encoded bytes; and transmitting, by one or more computer processors using one or more wireless communications components, the data stream to a recipient device.

In particular embodiments, the computer executable instructions for may further include instructions for determining, using the look-up table based on the one or more attributes of the first piece of healthcare data, a type of units for the first piece of healthcare data. In particular embodiments, the plurality of pieces of healthcare data comprises a data structure representing a patient encounter with a healthcare provider. In particular embodiments, the data structure comprises a first substructure comprising a first subset of the plurality of pieces of healthcare data comprising demographic data associated with a patient. In particular embodiments, the data structure comprises a second substructure comprising a second subset of the plurality of pieces of healthcare data comprising vital signs data associated with the patient.

A user-affixable device configured to transmit, receive, and store healthcare data, according to various embodiments, may include: a bandage comprising an adhesive portion, an absorbent portion, and a water-resistant flexible encapsulation portion, wherein the water-resistant flexible encapsulation portion is configured to encapsulation plurality of electronic components, and wherein the plurality of electronic components comprises: a microprocessor; data storage media communicatively connected to the microprocessor; a near-field communications (NFC) processor communicatively connected to the microprocessor; an NFC antenna communicatively connected to the NFC processor, wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device; transmit an activation signal to the microprocessor; a power supply configured to supply power to the microprocessor; a Bluetooth processor communicatively connected to the microprocessor; and a Bluetooth antenna communicatively connected to the NFC Bluetooth processor; wherein the microprocessor is configured to, at least partially in response to receiving the activation signal from the NFC processor, provide power to the data storage media and the Bluetooth processor; and wherein the Bluetooth processor is configured to, at least partially in response to receiving power from the microprocessor, establish a Bluetooth communications session with a wireless communications device.

In particular embodiments, the NFC processor is further configured to: detect a breaking of the NFC field; and at least partially in response to detecting the breaking of the NFC field, transmit a deactivation signal to the microprocessor. In particular embodiments, the microprocessor is further configured to: at least partially in response to receiving the deactivation signal from the NFC processor, cease providing power to the data storage media and the Bluetooth processor. In particular embodiments, the Bluetooth processor is further configured to: detect a termination of the Bluetooth communications session with the wireless communications device; and at least partially in response to detecting the termination of the Bluetooth communications session with the wireless communications device, transmit a deactivation signal to the microprocessor. In particular embodiments, the microprocessor is further configured to: at least partially in response to receiving the deactivation signal from the Bluetooth processor, cease providing power to the data storage media and the Bluetooth processor. In particular embodiments, the wireless communications device is a device distinct from the NFC initiator device. In particular embodiments, the Bluetooth processor is configured to, at least partially in response to receiving power from the microprocessor, transmit a message to the NFC initiator device indicating that the user-affixable device has Bluetooth capabilities. In particular embodiments, the Bluetooth processor is configured to establish the Bluetooth communications session with the NFC initiator device via the Bluetooth antenna. In particular embodiments, the Bluetooth processor is configured to: receive healthcare data via the Bluetooth antenna; and transmit the healthcare data to the microprocessor for storage at the data storage media.

A smart bandage system for processing healthcare data, according to various embodiments, may include: an adhesive means for adhering the smart bandage system to skin of a human patient; an absorbent means for absorbing moisture from the human patient; a flexible, water-resistant encapsulation means for housing a plurality of electronic components; a computer processing means for processing healthcare data and for providing power to one or more of the plurality of electronic components at least partially in response to receiving an activation signal from short-range wireless communications means; a data storage means for storing healthcare data; the short-range wireless communications means for communicating with one or more short-range wireless initiator devices using short-range wireless communications and for transmitting the activation signal to the computer processing means upon establishing short-range wireless communications session with the one or more short-range wireless initiator devices; a battery means for supplying power to the microprocessor; and a Bluetooth communications means for communicating with one or more Bluetooth-capable devices and for, at least partially in response to receiving power from the computer processing means, establishing a Bluetooth communications session with the one or more NFC initiator devices.

A data processing system for processing healthcare data, according to various embodiments, may include: a housing; a moisture-resistant encapsulation portion configured within the housing; a microprocessor configured within the moisture-resistant encapsulation portion; data storage media configured within the moisture-resistant encapsulation portion and communicatively connected to the microprocessor; a near-field communications (NFC) processor configured within the moisture-resistant encapsulation portion and communicatively connected to the microprocessor; an NFC antenna configured within the moisture-resistant encapsulation portion and communicatively connected to the NFC processor, wherein the NFC processor is configured to: at least partially in response to receiving an NFC signal from an NFC initiator device via the NFC antenna, establish an NFC field with the NFC initiator device; and at least partially in response to establishing the NFC field with the NFC initiator device; transmit an activation signal to the microprocessor; a power supply configured within the moisture-resistant encapsulation portion and configured to supply power to the microprocessor; a wireless communications processor configured within the moisture-resistant encapsulation portion and communicatively connected to the microprocessor; and one or more wireless communications antennas configured within the moisture-resistant encapsulation portion and communicatively connected to the wireless communications processor; wherein the microprocessor is configured to, at least partially in response to receiving the first activation signal from the NFC processor, provide power to the data storage media and the wireless communications processor; and wherein the wireless communications processor is configured to, at least partially in response to receiving power from the microprocessor, establish a wireless communications session with a wireless communications device using the one or more wireless communications antennas.

In particular embodiments, the wireless communications processor is a Wi-Fi processor; the one or more wireless communications antennas are one or more Wi-Fi antennas; and the wireless communications session is a Wi-Fi communications session. In particular embodiments, the wireless communications processor is further configured to: receive a request for healthcare data at the wireless communications processor from the wireless communications device via the wireless communications session; transmit the request for the healthcare data from the wireless communications processor to the microprocessor; retrieve the requested healthcare data from the data storage media by the microprocessor; transmit the requested healthcare data from the microprocessor to the wireless communications processor; receive the requested healthcare data from the microprocessor at the wireless communications processor; and transmit the requested healthcare data from the wireless communications processor to the wireless communications device via the wireless communications session using the one or more wireless communications antennas. In particular embodiments, the requested healthcare data comprises a sequence of encoded bytes. In particular embodiments, the NFC processor is further configured to detect a breaking of the NFC field; and at least partially in response to detecting the breaking of the NFC field, the NFC processor is further configured to transmit a deactivation signal to the microprocessor. In particular embodiments, at least partially in response to receiving the deactivation signal from the NFC processor, the microprocessor is configured to transmit an instruction to the wireless communications processor to terminate the wireless communications session with the wireless communications device. In particular embodiments, the housing is a band suitable for attachment about a human arm or a human leg. In particular embodiments, the housing is a bandage suitable for attachment to human skin.

A method of operating a healthcare data processing system, according to various embodiments, may include: establishing, by a near-field communications (NFC) processor via an NFC antenna, an NFC field with an NFC initiator device, wherein the NFC processor and the NFC antenna are encapsulated in a moisture-resistant bandage housing; transmitting an activation signal from the NFC processor to a microprocessor, wherein the microprocessor is encapsulated in the moisture-resistant bandage housing; at least partially in response to receiving the activation signal from the NFC processor, providing power, by a battery via the microprocessor, to a Bluetooth processor and data storage media, wherein the battery, the Bluetooth processor, and the data storage media are encapsulated in the moisture-resistant bandage housing; at least partially in response to receiving power from the battery via the microprocessor, establishing, by the Bluetooth processor via one or more Bluetooth antennas, a Bluetooth communications session with the NFC initiator device; wherein the one or more Bluetooth antennas are encapsulated in the moisture-resistant bandage housing; exchanging data, by the Bluetooth processor using the one or more Bluetooth antennas, via the Bluetooth communications session with the NFC initiator device; detecting, at the Bluetooth processor via the one or more Bluetooth antennas, a termination of the Bluetooth communications session with the NFC initiator device; at least partially in response to detecting the termination of the Bluetooth communications session with the NFC initiator device, transmitting, from the Bluetooth processor, a deactivation signal to the microprocessor; and at least partially in response to receiving the deactivation signal from the Bluetooth processor, ceasing, by the microprocessor, providing power from the battery to the Bluetooth processor and the data storage media.

In particular embodiments, the method may also include establishing, by the Bluetooth processor using the one or more Bluetooth antennas, one or more Bluetooth sessions with one or more respective health data sensors configured on a human user; receiving, via the one or more Bluetooth sessions with the one or more respective health data sensors, by the Bluetooth processor using the one or more Bluetooth antennas, health measurement data; transmitting, from the Bluetooth processor to the microprocessor, the health measurement data; receiving, at the microprocessor from the Bluetooth processor, the health measurement data; and storing, by the microprocessor, the health measurement data in the data storage media. In particular embodiments, one or more of the one or more health data sensors is a sensor selected from a group consisting of: (a) a heart rate sensor; (b) a body temperature sensor; (c) a sweat sensor; (d) a biosensor; and (e) an environmental sensor. In particular embodiments, exchanging data via the Bluetooth communications session with the NFC initiator device comprises: retrieving, by the microprocessor, a subset of the health measurement data from the data storage media; transmitting the subset of the health measurement data from the microprocessor to the Bluetooth processor; receiving the subset of the health measurement data from the microprocessor at the Bluetooth processor; and transmitting the subset of the health measurement data from the Bluetooth processor to the NFC initiator device via the Bluetooth communications session with the NFC initiator using the one or more Bluetooth antennas.

BRIEF DESCRIPTION OF THE DRAWINGS

Various embodiments are described below. In the course of this description, reference will be made to the accompanying drawings, which are not necessarily drawn to scale, and wherein.

DETAILED DESCRIPTION

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Exemplary System

Figure 1:
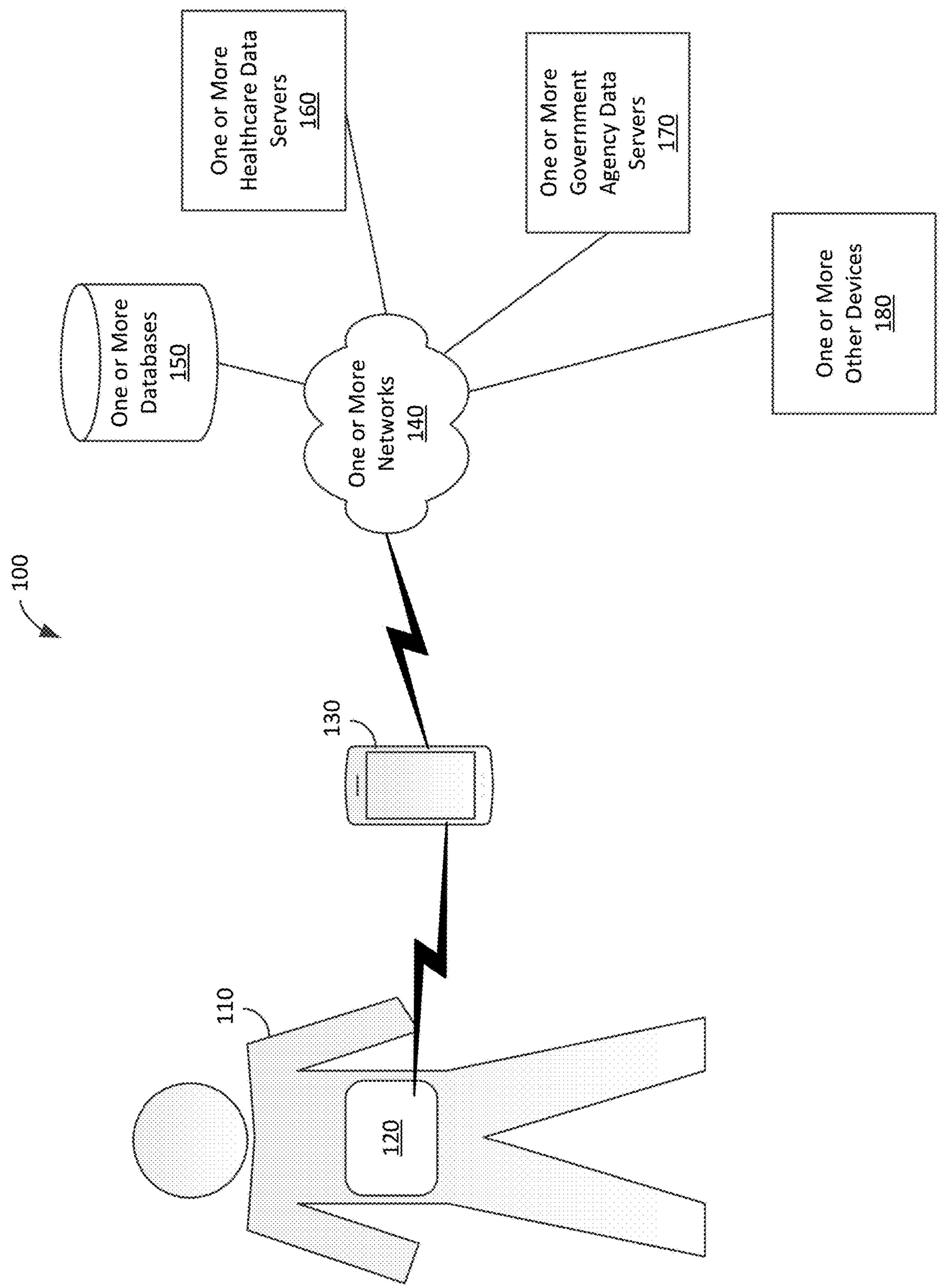
FIG. 1 is a diagram illustrating an exemplary system in which various embodiments may be implemented.

FIG. 1 illustrates an exemplary system 100 in which various embodiments may be implemented. In system 100, a patient 110 may be experiencing some type of medical issue. For example, the patient 110 may be experiencing a serious condition that renders the patient 110 unconscious or otherwise unable to communicate with healthcare providers, such as a traumatic injury or a debilitating illness (e.g., viral infection, bacterial infection, etc.). Note that animal patients (as opposed to human patients) are also contemplated herein and are typically incapable of substantive communication with human healthcare providers. In other examples, the patient 110 may be less affected by illness or injury, or may not be affected at all. In still other examples, the patient 110 may be any individual in a healthcare system where healthcare data and other related information may be of use to those providing healthcare to the patient 110. In such situations, the patient 110 may not be able to provide his or her own healthcare data due to incapacity and/or inability to easily recite such data. Furthermore, the healthcare providers attending to the patient 110 may not have immediate access to remote computing devices, network connectivity, etc. in order to retrieve the patient 110's healthcare data, for example, where such healthcare providers are operating in DIL conditions.

A smart bandage 120 (e.g., as described herein according to various embodiments) may be affixed to the patient 110.

As described in more detail herein, the smart bandage 120 may include various components (e.g., electronic components) and may execute various modules to facilitate the collection, storage and processing of healthcare data and other information that may, for example, be associated with the patient 110. The smart bandage 120 may include one or more bandage components that may serve to cover one or more wounds and/or to absorb moisture and/or liquids, such as those excreted by the patient 110. In particular embodiments, the smart bandage 120 may serve as a healthcare data storage and processing apparatus and may perform data compression and wireless communications as described herein.

A healthcare provider or other user may operate a mobile device 130 to wirelessly communicate with the smart bandage 120. The mobile device 130 may be any type of mobile computing device that may interact with a smart bandage, such as, but not limited to, a non-smart mobile phone, a dedicated healthcare data processing device, a smart phone, a laptop computer, a tablet computer, etc. The mobile device 130 may be any type of mobile computing device that is capable of communicating with another device (e.g., the smart bandage 120) using wireless communications technology, such as NFC, Wi-Fi, Bluetooth, and/or any other short-range wireless communications technology. Using a suitable wireless communication means (e.g., near field communications (NFC), Bluetooth, Wi-Fi, any other form of short-range wireless communications, etc.), the mobile device 130 may wirelessly transmit data to and/or receive data from the smart bandage 120, as described in more detail herein. The mobile device 130 may use various data compression techniques (such as those described herein) in order to compress, transmit, and store healthcare data more efficiently on the smart bandage 120. The mobile device 130 may also, or instead, use the decompression techniques described herein with healthcare data received from the smart bandage 120 in order to process, store, and/or transmit such data.

The mobile device 130 may be configured to communicate with one or more other devices via one or more networks 140 that may include any type of network and any combination of multiple networks. For example, the one or more networks 140 may include, but are not limited to, a wireless communications network (e.g., 3G, 4G, 5G, CDMA, etc.), a wireless local area network (WLAN) (e.g., Wi-Fi, etc.), a wired network (e.g., local area network (LAN), a wide area network (WAN), etc.), and/or any other type of communications network.

The mobile device 130 may communicate with any of a variety of other devices via one or more networks 140. Such devices may include, but are not limited to, one or more databases 150 that may store healthcare data and related data, one or more healthcare data servers 160 that may store and/or process healthcare data and related data, one or more government agency data servers 170 that may store and/or process healthcare data and related data on behalf of a government agency (e.g., Department of Defense, etc.), and any one or more other devices 180 that may store and/or process healthcare data and related data.

In various embodiments, the mobile device 130 may communicate with one or more other device via the one or more networks 140 at a different time than when the mobile device 130 to communicate with the smart bandage 120. For example, a user may first use mobile device 130 to communicate with the smart bandage 120 in a DIL environment and then later upload data retrieved from the smart bandage 120 to another device when the user is in a non-DIL environment (e.g., an environment with Internet connectivity). Similarly, a user may download data from one or more various devices while operating the mobile device 130 in a non-DIL environment and later, when working with the patient 110 in a DIL environment, use such data in communication exchanges with the smart bandage 120.

Exemplary Computer Architecture

Figure 2:
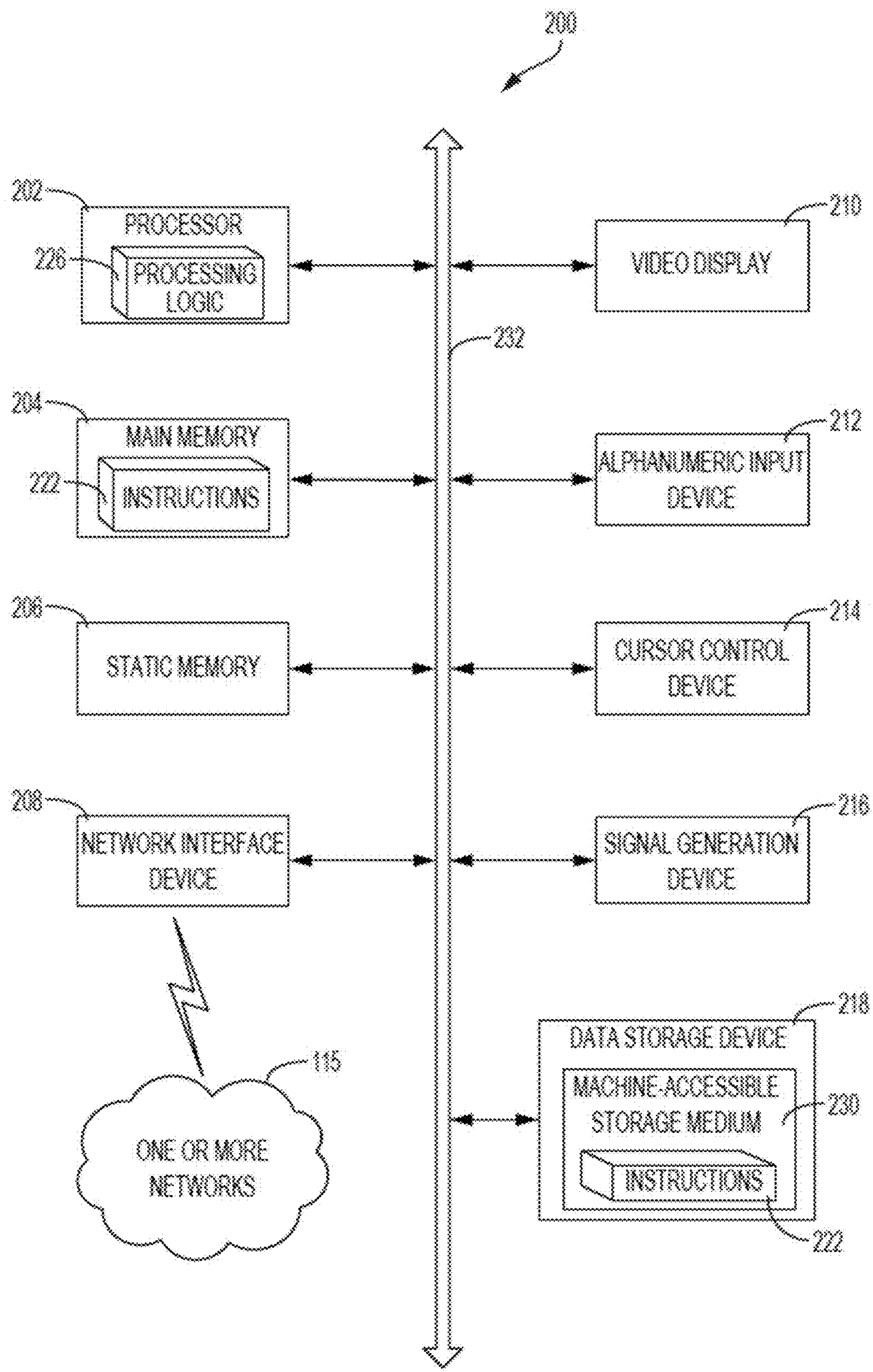
FIG. 2 is a diagram illustrating an exemplary computer that may be used in one or more exemplary system in which various embodiments may be implemented, such as exemplary system 100 of FIG. 1.

FIG. 2 illustrates a diagrammatic representation of a computer architecture of a computer 200 that may be used within a bandage, sticker, band, or other similar device for storing and transmitting large amounts of data and to implement structured and configurable data compression, for example, as described herein. In particular embodiments, the computer 200 may be suitable for use as a computer disposed within a bandage, sticker, or band as described herein that is configured to receive input from a device, sensors, etc. and store, process, and transmit such data.

In particular embodiments, the computer 200 may be connected (e.g., networked) to other computers using Bluetooth, NFC, another form of short-range wireless communications, and/or other wireless communications technologies. The computer 200 may also, or instead, connect to other computers using a LAN, an intranet, an extranet, and/or the Internet. The computer 200 may be, or may be based on, any type of device having one or more processors and data storage capabilities and capable of executing a set of instructions (sequential or otherwise) that specify actions to be taken by that computer. Further, while only a single computer is illustrated, the term "computer" shall also be taken to include any collection of computers that individually or jointly execute a set (or multiple sets) of instructions to perform any one or more of the methodologies discussed herein, such as the data compression and/or decompression methods described in more detail below.

The computer 200 may include a processing device 202 (e.g., one or more computer processors) and a main memory 204 (e.g., read-only memory (ROM), random access memory (RAM), flash memory, dynamic random access memory (DRAM) such as synchronous DRAM (SDRAM) or Rambus DRAM (RDRAM), etc.) storing instructions 222 that may be executed by the processor 202. The computer 200 may also include a static memory 206 (e.g., flash memory, static random-access memory (SRAM), etc.) and a data storage device 218. All such components of the computer 200 may communicate with each other via a bus 232.

The processor 202 represents one or more general-purpose processing devices such as a microprocessor, a central processing unit, and the like. More particularly, each processing device of the processor 202 may be a complex instruction set computing (CISC) microprocessor, reduced instruction set computing (RISC) microprocessor, very long instruction word (VLIW) microprocessor, Scalar Board, a processor implementing other instruction sets, or a processor implementing a combination of instruction sets. Each processing device of the processor 202 may also, or instead, be one or more special-purpose processing devices such as an application specific integrated circuit (ASIC), a field programmable gate array (FPGA), a digital signal processor (DSP), a network processor, and the like. The processor 202 may be configured to execute processing logic 226 for performing various operations and steps discussed herein.

The computer 200 may further include a network interface device 208 that may include one or more NFC components, Bluetooth components, any other type of short-range wireless communications components, and/or any other wireless communications components that may allow communication directly with any other device (e.g., a smart bandage) and/or via any type of network. The computer 200 also may include a video display unit 210 (e.g., a flexible computer display, a liquid crystal display (LCD), an LED display, or any other suitable display), an alphanumeric or other type of input device 212 (e.g., a keyboard, a touch-screen, etc.), a cursor control or other input device 214 (e.g., touch-sensitive input device, or other suitable input device, etc.), and a signal generation device 216 (e.g., a speaker).

The data storage device 218 may include a non-transitory computer-accessible storage medium 230 (also known as a non-transitory computer-readable storage medium or a non-transitory computer-readable medium) on which may be stored one or more sets of instructions (e.g., software 222) embodying any one or more of the methodologies or functions described herein. The software 222 may also reside, completely or at least partially, within the main memory 204 and/or within the processor 202 during execution thereof by the computer 200. The main memory 204 and the processing device 202 may also constitute computer-accessible storage media. The software 222 may further be transmitted or received directly from another device and/or over a network (e.g., one or more networks 140) via the network interface device 208.

While the computer-accessible storage medium 230 is shown in an exemplary embodiment to be a single medium, the terms "computer-accessible storage medium," "computer-readable storage medium," and "computer-readable medium" should be understood to include a single medium or multiple media (e.g., a centralized or distributed database and/or associated caches and servers) that store the one or more sets of instructions. The terms "computer-accessible storage medium," "computer-readable storage medium," and "computer-readable medium" should also be understood to include any medium that is capable of storing, encoding, or carrying a set of instructions for execution by the computer and that cause the computer to perform any one or more of the methodologies of the present invention. The terms "computer-accessible storage medium," "computer-readable storage medium," and "computer-readable medium" should accordingly be understood to include, but not be limited to, solid-state memories, optical media, magnetic media, etc.

Also, while the computer 200 is shown in FIG. 2 as including various components, it should be understood that the computer 200 may include greater or fewer components in other embodiments. For example, in certain embodiments 200, the computer may not include a video display 210, signal generation device 216, or other components shown in FIG. 2.

Smart Bandage Overview

In most modern industries and businesses, storing and transmitting large amounts of data using computing devices and networks is common. The healthcare industry is no exception and the use of modern computing devices and networks has greatly increased the efficacy of modern healthcare. However, situations may arise where the communication of healthcare data beyond the immediate area is much more limited or even impossible, such as in "disconnection, intermittent, or low-bandwidth" (DIL) environments (e.g., battlefields, remote operations, temporary hospitals, emergency facilities, in natural disasters, any other situations where the normal infrastructure has been rendered inoperable, etc.). In such situations, the need to collect, store, and exchange healthcare information remains. To accommodate data storage needs in such difficult environments, the various disclosed embodiments provide for a device that can store and transmit large amounts of data quickly and securely, especially to support situations where direct device to device transmission is limited or (e.g., practically) impossible.

In DIL situations, healthcare providers may be operating in a temporary medical facility (e.g., in an operational battlefield, in a temporary medical facility set up to address a pandemic, in a temporary medical facility set up to address a natural disaster, etc.). In such environments, healthcare providers may need to treat patients at the point of injury and/or at the location where they experienced an onset of illness (e.g., wounded soldiers in the battlefield, victims of natural disaster proximate to the impact of the disaster, victims of disease (e.g., viral and/or bacterial infection) at the location of symptom onset, etc.). Often in these scenarios, the healthcare providers and others are operating in forward deployed situations where there is little or no access to high speed communications technologies.

Various embodiments provide specialized solutions that allow a healthcare provider operating in such DIL environments to digitally capture medical information on a mobile device and document the care of an injured or ill patient. In various embodiments, the healthcare provider may convey the medical information physically along with the patient as the patient moves from the forward operating environment to a brick and mortar hospital or other, more permanent, medical facility. Various disclosed systems and methods provide for a device that is easy to use, can be affixed to, and move with, the patient, and can carry sufficient amounts of data (e.g., pictures, video, medical records, recordings, etc.) to improve the information available about the care received by the patient and prevent important medical data from lagging behind the patient.

In various embodiments, the disclosed apparatus may be used in DIL environments and may be configured to be affixed to a patient. In particular embodiments, the disclosed apparatus may serve at least one other purpose, such as also functioning as a bandage. Various embodiments may be configured to store relatively large amounts of data and to transmit, receive, read, and/or present such data as the patient moves along various points in the path of care, for example, from point of injury to a hospital or other care location. While various embodiments set forth herein may be described using examples related to providing medical care to an injured or ill patient in a DIL environment, various embodiments of the disclosed systems and methods may be implemented in any suitable situations and environments, and implemented in any suitable systems and configurations, such as, but not limited to, equipment tags, engine maintenance tags, medical products, and/or any other devices and systems that may electronically store maintenance records and/or a history of how an associated item has been handled. Various embodiments of the disclosed systems and methods may allow a record associated with an item to be affixed to, and travel with, the item itself without requiring the use of a centralized database or network communications to retrieve the information in such a record.

Smart Bandage System and Apparatus

Figure 3:
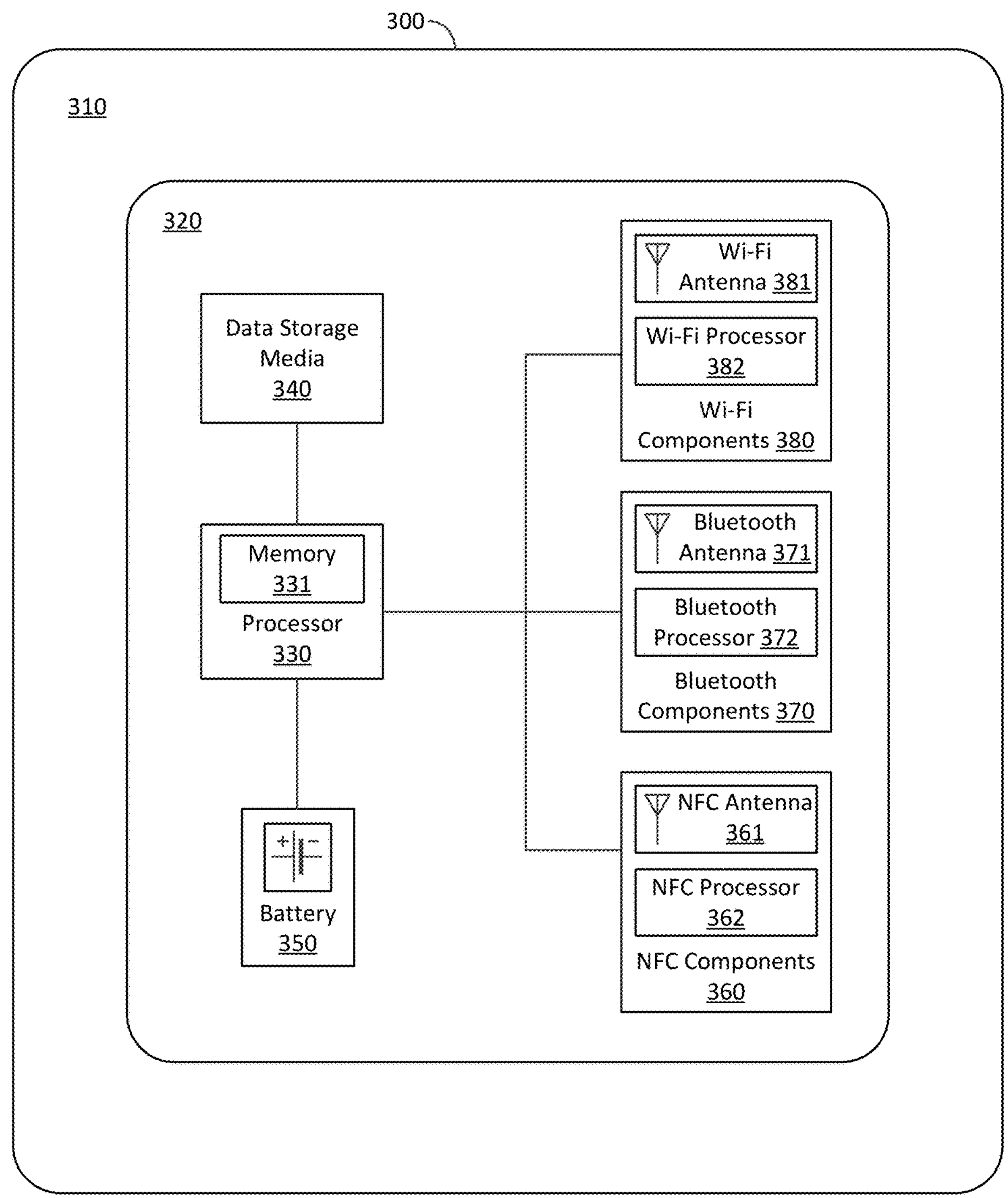
FIG. 3 is a diagram illustrating an exemplary smart bandage in which various embodiments may be implemented.

FIG. 3 illustrates a block diagram representing an exemplary smart bandage 300. Note that, while the embodiments described herein may be referred to for explanatory purposes as a "bandage," various embodiments may be take the form of a bandage, sticker, tag, label, band (e.g., wrist band, ankle band, leg band, etc.), or other device, system, or apparatus that may be configured according to one or more of the disclosed embodiments. In various embodiments, the smart bandage 300 may be configured to encapsulate the various electronic components of the system (e.g., components to transmit, receive, and/or store data) and the connections therebetween. In particular embodiments, the smart bandage 300 may be implemented as a bandage that may be used in an operational battlefield environment or other DIL environment to carry patient data while physically attached to the patient. The smart bandage 300 may have a size of about 2×2 inches, 4×4 inches, or any other suitable size. The smart bandage 300 may include typical bandage and/or sticker components, such as an adhesive section 310 that may be configured to adhere to a patient or some other object. In particular embodiments where the smart bandage 300 serves as a bandage, the bandage section 320 may be configured with absorbent material designed to absorb liquids that may emanate from a wound or sore. The bandage section 320 may also encapsulate, according to particular embodiments, the various electronic components described below in a waterproof or water-resistant housing. The bandage section 320, including any waterproof or water-resistant housing encompassing one or more electronic components, may be flexible and allow for the use of the smart bandage 300 as a wound dressing. In alterative embodiments, one or more of the various electronic components may be disposed on the outside of the bandage.

As a particular example, the electronic components enclosed in the section 320 may be embedded into the bandage such that the smart bandage 300 may have dual utility to a field medic in that the smart bandage 300 may serve as a bandage for covering one or more wounds and also provide the capability of transmitting and storing patient medical data. In particular embodiments where the smart bandage 300 is used as a bandage, the smart bandage 300 may receive patient medical data from a mobile device operated by a first healthcare provider, store the patient medical data, and transmit the patient medical data to a mobile device operated by a second healthcare provider. By using the smart bandage 300 as a bandage, a healthcare provider may not need to use multiple bandages for a patient or use a separate device to move patient medical data with the patient from one point of care to another (e.g., from the point of injury to the hospital). Various embodiments may also reduce the training that may otherwise be needed in the operation of a separate patient medical data capture device (e.g., if patient medical capture was performed using a device that was separate from a bandage and/or dedicated to patient medical data capture). In various non-medical embodiments, encapsulating the components of the disclosed systems in a sticker or bandage may facilitate the use of the system in other contexts by allowing the disclosed embodiments to be affixed to various items, devices, equipment, etc. and thereby enabling the system to easily travel with the object to which the system is affixed. In various embodiments, the components of the disclosed systems may be encapsulated in a band that may be worn by a human or animal in a medical or non-medical context, for example, worn around the wrist, ankle, leg, or arm of a wearer of such a band.

In various embodiments, the smart bandage 300 (or other wearable smart device) includes a processor 330 that may be communicatively connected to one or more of the other components withing the bandage section 320. In particular embodiments, the processor 330 may be coupled to, or otherwise include, a memory 331 of any suitable type. The system may include operating system software embedded on the processor 330 (e.g., stored in the memory 331 of the processor 330). For data storage, the smart bandage 300 may be configured with a data storage media 340 as described herein. The data storage media 340 may be any type of data storage media suitable for storing relatively large amounts of data, such as healthcare data (e.g., a solid-state storage media device of any type). The smart bandage 300 may also be configured with a battery 350 for providing power to the processor 330. The battery 350 may be any suitable portable power supply capable of providing power to the electrical components of the smart bandage 300. The battery 350 may provide power to the other electrical components of the smart bandage 300, either directly or via the processor 330.

In various embodiments, the smart bandage 300 may comprise one or more NFC components 360 that may include one or more of an NFC antenna 361 and/or an NFC processing chip 362. The NFC components 360 may be communicatively connected to the processor 330. While the NFC components 360 may receive power wirelessly from an external mobile device (e.g., as in a typical NFC operation), the NFC components 360 may also, or instead, draw power from the battery 350 directly or via the processor 330.

In various embodiments, the smart bandage 300 may also, or instead, be configured with one or more Bluetooth communications components 370 that may include one or more of a Bluetooth antenna 371 and/or a Bluetooth processing chip 372. The Bluetooth components 370 may be communicatively connected to the processor 330. The Bluetooth components 370 may draw power from the battery 350 directly or via the processor 330. In particular embodiments, the Bluetooth components 370 may also, or instead, receive power wirelessly (e.g., similar to NFC components).

In various embodiments, the smart bandage 300 may be configured to communicate using IEEE 802.11 wireless technologies and/or Wi-Fi Alliance technologies, commonly referred to as "Wi-Fi." In such embodiments, the smart bandage 300 may also, or instead, be configured with one or more Wi-Fi communications components 380 that may include one or more of a Wi-Fi antenna 381 and a Wi-Fi processing chip 382. The Wi-Fi components 380 may be communicatively connected to the processor 330. The Wi-Fi components 380 may draw power from the battery 350 directly or via the processor 330. In particular embodiments, the Wi-Fi components 380 may also, or instead, receive power wirelessly (e.g., similar to NFC components).

In various embodiments, the smart bandage 300 may also, or instead, be configured with one or more other types of wireless communications components that may include any suitable one or more wireless communications antennas and wireless communications processors. Such one or more wireless communications may be communicatively connected to the processor 330. These wireless communications components may draw power from the battery 350 directly or via the processor 330. In particular embodiments, these wireless communications components may also, or instead, receive power wirelessly (e.g., similar to NFC components).

In various embodiments, the smart bandage 300 may serve as an improved type of NFC tag that has much greater storage and communications capabilities for processing information, such as, but not limited to, healthcare information. The smart bandage 300 may integrate NFC capabilities while addressing the limitations of typical NFC devices, such as limited storage space and communications capabilities. In various embodiments, the smart bandage 300 utilizes the NFC components 360 to establish one or more communication channels with at least one other device (e.g., a mobile phone, a laptop, a tablet computer, etc.) to transmit and receive data (e.g., healthcare data) that can be stored on the system itself.

NFC Antenna and Processing Chip as on/Off Switch in a Smart Bandage

Typical NFC tags and devices derive their power from a field generated between an initiator device (e.g., a smartphone) and the NFC device. Via this field, a small NFC chip within the NFC device receives instructions to transmit its small data payload to the initiator device and/or receive data from the initiator device. The power available to typical NFC devices may be quite small because the generated field is their sole source of power. Therefore, the amount of processing that such devices may perform may be very limited.

In various embodiments, the processor 330 of the smart bandage 300 is capable of running much more complex algorithms than a typical NFC device and has access to the much larger data storage capacity of the data storage media 340 as well as its own memory 331. This is due, at least in part, to the processor 330 being coupled to an independent, stand-alone power supply, the battery 350. While the battery 350 may supply power to any of the electronic components of the smart bandage 300, in various embodiments the battery 350 may be configured to not power the components of the smart bandage 300 continuously in order to minimize the use of power by the smart bandage 300. This may enable longer term access and storage of information so that such information is accessible to other devices for a sustained amount of time.

In various embodiments, the system may use the NFC components 360, and particularly the NFC antenna 361, as an on/off switch for the internal power supply of the smart bandage 300 (e.g., the battery 350). The smart bandage 300 may receive a signal from an NFC initiator device (e.g., a smartphone) via the NFC antenna 361 and may, in response to detecting the signal at the NFC antenna 361, establish an NFC field with NFC initiator device using the NFC components 360. In response to establishing this NFC field, the NFC components 360 may transmit a signal to the processor 330 instructing the processor 330 to "turn on" and/or "boot up." The processor 330 may activate the battery 350 to supply greater, continuous power to the processor 330 and to the other components of the smart bandage 300. In response to establishing this NFC field, the NFC components 360 may also, or instead, transmit a signal directly to the battery 350 instructing the battery 350 to turn on and thereby send power to the processor 330 that causes the processor 330 to boot up. The processor 330 in conjunction with the battery 350 may then supply greater, continuous power to the other components of the smart bandage 300.

After activating using the power supplied by the battery 350, the processor and other components of the smart bandage 300 may then stay powered for as long as the initiator device maintains contact with the NFC components 360. While in contact with the initiator device, the smart bandage 300 may exchange data using NFC, but process and/or otherwise handle the data using the processor 330 and the other components of the smart bandage 300. For example, the smart bandage 300 may receive data for storage from the initiator device via NFC using the NFC components 360, process the data using the processor 330, and store the processed data on the data storage media 340. Similarly, the smart bandage 300 may receive an instruction to provide stored data from the initiator device via NFC and, in response, may retrieve the data from the data storage media 340, process the data as needed at the processor 330, and transmit the data to the initiator device via NFC using the NFC components 360.

In various embodiments, in response to the initiator device being removed and/or the NFC field being broken between the initiator device and the smart bandage 300, the NFC processor 362 may automatically power down the processor and any other powered components of the smart bandage 300, or otherwise instruct such components to power down, thereby conserving battery power.

Using Bluetooth Components in Conjunction with NFC Components in a Smart Bandage In various embodiments, the smart bandage 300 may include one or more Bluetooth components 370 that may include one or more of a Bluetooth antenna 371 and/or Bluetooth processor 372. The Bluetooth components 370 may use any suitable version and/or specification of Bluetooth. In particular embodiments, the Bluetooth components 370 use Bluetooth Low Energy (BT LE) and Bluetooth Specification 5.0 or later. By using the Bluetooth components 370 in conjunction with the NFC components 360, the smart bandage 300 may achieve higher transfer speeds and/or may not require a continuous NFC field maintained by an NFC initiator device for operation.

In various embodiments, NFC may be used to "wakeup" the smart bandage 300 as described above, when an NFC initiator device establishes an NFC field with the NFC components 360 of the smart bandage 300. In response to the smart bandage 300 detecting the NFC initiator device, the NFC components 360 boot the processor 330 and power the data storage media 340 and the Bluetooth components 370, enabling the Bluetooth components 370 to transmit and receive data. The NFC components 360 may then transmit a specialized NFC Data Exchange Format (NDEF) message to the initiator device that indicates that the smart bandage 300 has Bluetooth capabilities and can use BT LE to transfer data instead of using NFC. This specialized message may include a BT LE device address associated with the Bluetooth components 370. If the initiator device is Bluetooth enabled, it can use the BT LE address transmitted by the smart bandage 300 to "bond" to the Bluetooth components 370. Using a customized handshake of proprietary commands, the initiator device may inform the smart bandage 300 via Bluetooth that the initiator device wants to read data from the smart bandage 300 and/or inform the smart bandage 300 via Bluetooth that the initiator device wants to write data to the smart bandage 300.

If the initiator device is in read mode (e.g., has instructed the smart bandage 300 to transmit stored data), the smart bandage 300 may retrieve data from the data storage media 340 and transmit the retrieved data to the initiator device using the Bluetooth generic attribute (GATT) profile via the Bluetooth components 370. When the smart bandage 300 completes sending the requested data using the Bluetooth components 370, the smart bandage 300 may transmit a termination command (e.g., a proprietary command) to the initiator device via the Bluetooth components 370 to inform the initiator device that all requested data has been sent.

If the initiator device is in write mode (e.g., has instructed the smart bandage 300 to receive and store data), the initiator device will transmit the data to the smart bandage 300 via Bluetooth and the smart bandage 300 will receive the data using the Bluetooth components 370. The smart bandage 300 will process the received data as needed and store the received data in the data storage media 340. When the initiator device has completed transmitting the data to be stored to the smart bandage 300, the initiator device will transmit an end-of-transmission command to the smart bandage 300.

When the interaction (e.g., read or write) with the initiator device via Bluetooth is complete, the BT LE bond may be broken. In response to the breaking of this bond, the Bluetooth components 370 may be configured to return the smart bandage 300 to a “sleep” or low power mode by instructing the processor 330 and any other powered components of the smart bandage 300 to power down, thereby conserving the power stored by the battery 350.

Using Wi-Fi Components in Conjunction with NFC Components in a Smart Bandage

In various embodiments, the smart bandage 300 may include one or more Wi-Fi components 380 that may include one or more of a Wi-Fi antenna 381 and/or Wi-Fi processor 382. The Wi-Fi components 380 may use any suitable version and specification of any wireless communications technology, such as IEEE 802.11. By using the Wi-Fi components 380 in conjunction with the NFC components 360, the smart bandage 300 may achieve higher transfer speeds and/or may not require a continuous NFC field maintained by an NFC initiator device for operation.

In various embodiments, NFC may be used to “wakeup” the smart bandage 300 as described above, in response to an NFC initiator device establishing an NFC field with the NFC components 360 of the smart bandage 300. When the smart bandage 300 detects the NFC initiator device, the NFC components 360 boot the processor 330 and power the data storage media 340 and the Wi-Fi components 380, enabling the Wi-Fi components 380 to transmit and receive data. The NFC components 360 may then transmit a specialized NFC Data Exchange Format (NDEF) message to the initiator device that indicates that the smart bandage 300 has Wi-Fi capabilities and can use Wi-Fi to transfer data instead of using NFC. This specialized message may include a device MAC address associated with the one or more Wi-Fi components 380. If the initiator device is Wi-Fi enabled, it can use the MAC address associated with the Wi-Fi components 380 transmitted by the smart bandage 300 (e.g., directly or via a Wi-Fi router) to establish an Internet Protocol (IP) communications session with the smart bandage 300 using the Wi-Fi components 380. The initiator device may inform the smart bandage 300 via this communications session that the initiator device wants to read data from the smart bandage 300 and/or inform the smart bandage 300 via this communications session that the initiator device wants to write data to the smart bandage 300.

If the initiator device is in read mode (e.g., has instructed the smart bandage 300 to transmit stored data), the smart bandage 300 may retrieve data from the data storage media 340 and transmit the retrieved data to the initiator device using the Wi-Fi components 380. When the smart bandage 300 completes sending the requested data using the Wi-Fi components 380, the smart bandage 300 may terminate the communications session via the Wi-Fi components 380 and/or inform the initiator device that all requested data has been sent.

If the initiator device is in write mode (e.g., has instructed the smart bandage 300 to receive and store data), the initiator device will transmit the data to the smart bandage 300 via the IP communications session and the smart bandage 300 will receive the data using the Wi-Fi components 380. The smart bandage 300 will process the received data as needed and store the received data in the data storage media 340. When the initiator device has completed transmitting the data to be stored to the smart bandage 300, the initiator device may terminate the communications session and/or inform the smart bandage 300 that all data has been sent.

As noted above, in response to determining that the interaction (e.g., read or write) with the initiator device via Wi-Fi is complete, the system may terminate the communications session. In response to the termination of the communications session using Wi-Fi, the Wi-Fi components 380 may be configured to return the smart bandage 300 to a “sleep” or low power mode by instructing the processor 330 and any other powered components of the smart bandage 300 to power down, thereby conserving the power stored by the battery 350. In particular embodiments, in response to detecting the breaking of the NFC bond with the NFC initiator device, the NFC components 360 may transmit a deactivation signal to the processor 330, which may, in response, transmit a signal to the Wi-Fi components 380 to terminate the Wi-Fi communications session and then power down.

In particular embodiments, any of the described wireless communications technologies may be used in combination with short-range wireless communications technologies other than NFC. For example, one or more short-range wireless communications components (e.g., one or more non-NFC short-range wireless communications components) may establish a short-range wireless communications session (e.g., a non-NFC short-range wireless communications session) with one or more remote computing devices. In response to establishing this communications session, the one or more short-range wireless communications components may transmit an activation signal to one or more Wi-Fi and/or Bluetooth components. In response to the termination of this communications session, the one or more short-range wireless communications components may transmit a deactivation signal to the one or more Wi-Fi and/or Bluetooth components. The system may perform these and other aspects described herein using any alternative, non-NFC short-range wireless communications technology.

Transmitting and Receiving Large Amounts of Data Using NFC on a Smart Bandage

As noted herein, current NFC devices are very limited in the amount of data they can store, largely due to the limited power available to such devices due to using an NFC field as a power source. In various embodiments, by using an on-board power supply such as the battery 350, a processor such as the processor 330, and storage components such as the data storage media 340, the disclosed embodiments may provide much greater data storage capacity. To further increase the data storage capabilities of the disclosed embodiments, the smart bandage 300 may use one or more methods and/or algorithms based on current NFC technology that allow the smart bandage 300 to emulate a standard Type2 NFC tag. By using such tag emulation, the processor 330 may be able to communicate, via the NFC components 360, with an initiator device to send and/or receive data using “chunks” that are constrained by the limitations and data transfer speeds of NFC technology. The processor 330 may use this method to continually receive and/or transmit data via these chunks between the smart bandage 300 and the initiator device until all required data is sent and/or received.

While the smart bandage 300 is writing data to the data storage media 340 (e.g., receiving data from the initiator device and storing the data to the data storage media 340), the smart bandage 300 may use the processor 330 and a chunking algorithm to write data to the data storage media 340, saving each chunk as it is successfully received. The processor 330 may monitor the storage of such data at the data storage media 340 for success or failure and transmit the appropriate NFC commands back to the initiator device to confirm whether the data has been written successfully or not.

While the smart bandage 300 is reading data from the data storage media 340 (e.g., retrieving data from the data storage media 340 and transmitting the retrieved data to the initiator device), the smart bandage 300 may use the processor 330 and a chunking algorithm to read data from the data storage media 340 and transmit that data using a maximum data chunk size and the current NFC transmission capabilities to the initiator device. The processor 330 may monitor the success or failure of this data transfer process and may transmit the appropriate NFC commands back to the initiator device to confirm whether the data has been retrieved and transmitted successfully or not.

Security and Encryption of Data Stored on a Smart Bandage

Current NFC technology uses NFC tags that lack the ability to encrypt data (e.g., on the fly) and therefore any device capable of activating a current NFC device can read the data stored on the NFC device. However, the smart bandage 300, because it includes the processor 330, the data storage media 340, and the on-board power supply battery 350, may programmatically encrypt data, for example as it is received, processed, and/or transmitted. Therefore, the disclosed embodiments may be configured for specific users (e.g., customers, government, military, etc.) with unique encryption keys that may limit the ability of any device to read data from the smart bandage 300 without the appropriate keys or exchange of information. For example, should the smart bandage 300 be lost or stolen and end up in the hands of unauthorized users (e.g., enemy combatants, criminals) such unauthorized users would not be able to read data on the device.

Because various embodiments of the smart bandage 300 include a microprocessor such as the processor 330 and, in some examples, Bluetooth components such as the Bluetooth components 370, various disclosed embodiments may also serve as active data logging devices for biosensors that use BT LE capabilities. In various embodiments, the smart bandage 300 or other suitable smart wearable device, such as a patch, sticker, bandage, or band may be worn by a user (e.g., an active duty soldier) along with one or more other biosensors such as one or more of a heart monitor, a sweat monitor, a heat monitor, an environmental biosensor, and/or any other type of similar device (e.g., planned, in use, or envisioned to be worn by a soldier). The smart bandage 300 may connect to these biosensors and, because of its greater storage and processing capabilities, process and record readings from these sensors. A healthcare provider or monitor may then use a suitable computing device (e.g., a smartphone) to connect to and communicate with the smart bandage 300 as described herein to obtain readings collected from the sensors attached to the user (e.g., to assess a wearer's ongoing readiness and apply interventions as needed).

Because the smart bandage 300 may include one or more components having the ability to execute algorithms and code, the smart bandage 300 may use specific algorithms to measure and/or summarize one or more sensor readings, and/or to generate and transmit one or more alerts to a healthcare provider or suitable monitor via a mobile device communicating with the smart bandage 300. In a particular embodiment, the system may generate and transmit an alert in response to detecting a measurement or calculation that indicates that a problem has been detected with a wearer of the smart bandage 300. For example, the smart bandage 300 may execute an algorithm to capture sweat sensor data and calculate a quantity and/or salinity of the wearer's sweat. Using one or more predetermined values and/or thresholds, the smart bandage 300 may generate an alert that the wearer is dehydrated based on, for example, one or more changes in the volume of sweat that the wearer is producing and the calculated salinity of the wearer's sweat. The smart bandage 300 may transmit this alert to another device to notify that device's user (e.g., a healthcare provider or monitor) of the alert in response to the smart bandage 300 being activated by that device, for example, as described above.

In various non-military embodiments, various disclosed embodiments may alternatively be implemented as a personal wearable (e.g., a band, a patch, etc.) for people wearing one or more medical sensors that require long term observations at home or in a hospital, which may give such people much greater mobility as compared to wired monitoring devices or bulky worn monitoring devices currently in use. In other embodiments, athletes may wear one or more sensors and one or more versions of a smart bandage or other smart wearable device such as those discussed above during sporting events so that coaches or trainers can measure their medical signs. In particular embodiments, the components and functions of the smart bandage 300, and any of the disclosed systems and methods, may be implemented in implantable medical devices surgically implanted into a user and capable of one or more of the aspects described herein.

In a particular embodiment, a smart bandage or other smart wearable device as described herein may be used in a pandemic situation. For example, a patient reporting symptoms of a virus (e.g., COVID-19) may report to a hospital emergency room wherein healthcare providers may determine that the patient requires transport to a specialized medical facility. The healthcare providers at the emergency room may attach a smart bandage or other smart wearable device as described herein to the patient and load the smart bandage/device with information related to the patient's symptoms, diagnosis, and care provided thus far. The patient may then be transported to the specialized medical facility, where specialized healthcare providers may retrieve this patient's medical data and provide the appropriate care.

Smart Bandage Control Process

Figure 4:
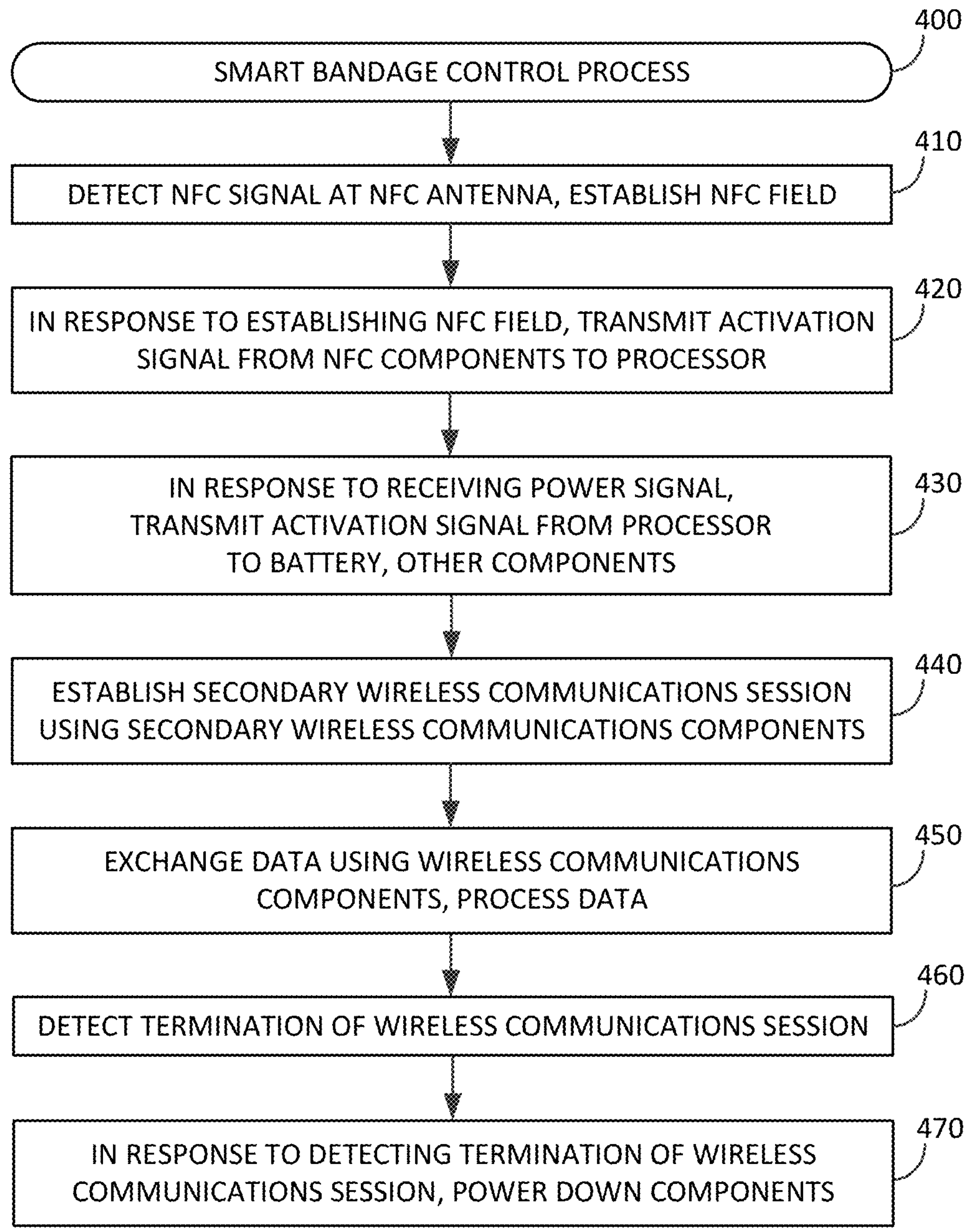
FIG. 4 is a flow chart showing an example of a smart bandage control process.

FIG. 4 illustrates an example Smart Bandage Control Process 400 that may be performed by a smart bandage, such as the smart bandage 300, according to various embodiments. In performing the Smart Bandage Control Process 400, the system begins at Step 410 where an NFC signal transmitted by an NFC initiator device may be detected by an NFC antenna configured at a smart bandage. In response to detecting the NFC signal, the one or more NFC components of the smart bandage may then establish an NFC field with the initiator device.

At Step 420, in response to successfully establishing the NFC field, one or more NFC components of the system, such as an NFC processor, may transmit an activation signal to a system processor. In particular embodiments, at Step 420 the NFC processor may also transmit an activation signal to one or more other components of the system, such as a battery or other power source.

At Step 430, in response to receiving the activation signal from the NFC processor, the system processor may transmit an activation signal to one or more other components of the smart bandage, or otherwise cause such components to power up. In particular embodiments, the processor may instruct the battery to power on, which may in turn provide power to one or more of the other components of the smart bandage, causing such components to power on.

At Step 440, secondary (e.g., non-NFC) wireless communications components of the smart bandage may attempt to establish a wireless communications session using their respective technology. In particular embodiments, the system may not be configured with any other wireless communications capabilities other than NFC. In such embodiments, Step 440 may be bypassed. In other particular embodiments, the system may be configured with secondary wireless communications components that may be one or more Bluetooth components, one or more Wi-Fi components, and/or one or more other wireless communications components, for example, as described above. At Step 440, the system, after powering such secondary wireless communications components at Step 430, may use the secondary wireless communications to establish a communications session that the system may use to wirelessly exchange data with another device (e.g., the NFC initiator device, any other device).

At Step 450, the system may exchange data wirelessly with one or more remote computing devices. The system may use one or more NFC components, Bluetooth components, Wi-Fi components, and/or other wireless communications components to perform this data exchange. Further at Step 450, the system may process the exchanged data in any suitable manner (e.g., store, transmit, compress, decompress, etc.).

At Step 460, the system may detect the termination of one or more wireless communications sessions. For example, the system may detect the breaking of the NFC field with the NFC initiator device, the breaking of a Bluetooth bond with another device, the termination of an IP or TCP communication session with another computing device, etc. At Step 470, in response to detecting the termination of the wireless communications session, the system may power down. In particular embodiments, the process may transmit one or more signals to each other component of the smart bandage that cause those components to power off.

In particular embodiments, the system may have multiple wireless communications sessions active at one time, as described above. For example, the system may initially establish an NFC field with an NFC initiator device and then establish a Bluetooth bond with a device (that may or may not be the NFC initiator device) for data exchange. In such embodiments, the termination of either or both such wireless communications sessions may cause the system processor to power down the system. For example, the system may be configured to maintain power to its components for the duration of an active NFC field, while establishing and terminating several Bluetooth bonds and/or Wi-Fi communications session while that NFC field is active, and only powering down its components when the NFC field is broken. In another example, the system may be configured to maintain power to its components for the duration of an active Bluetooth bond, regardless of whether an active NFC field is maintained, only powering down its components when the Bluetooth bond is broken. The system may be configured to power up and/or power down its components based on any combination of wireless communications session establishment and termination.

Structured and Configurable Data Compression—Overview

In modern computing environments, data may be exchanged between mobile devices, computers, and applications quickly and reliably using networks capable of transmitting large volumes of data at high speeds. Devices operating in such environments often include wireless capabilities that further increase the ease with which large amounts of data may be quickly exchanged. As discussed above, in most modern computer environments, there is usually little need to reduce or minimize the size, type, and structure of data being exchanged because the devices and the network used to exchange the data can typically transmit, receive, and store large volumes of data at low cost and without sacrificing the user experience. This has resulted in the proliferation of verbose and complex data structures and message formats. Such data structures and message formats are designed to exchange data between applications and allow computers to process and interpret the structures and messages into actionable records.

For example, in the medical space, computing devices may use the Health Level 7 (HL7) data structures and message formats to provide robust data exchange. HL7 is designed to facilitate the communication of medical information in a standardized manner using structured formats, allowing the movement and sharing of patient records between disparate medical applications and systems. In another example, systems may use data structures and message formats defined by the Fast Healthcare Interoperability Resources (FHIR) standard that use a common internet message structure (e.g., JavaScript Object Notation (JSON)) for formatting data that is to be exchanged over the Internet and/or via Web Services. The messages generated using such standards may be lengthy and consume large amounts of storage space. The devices processing such messages may use relatively large amounts of memory to represent the information contained in such messages. The size of such messages is largely due to the manner in which the information within the messages is encoded and the structural nature of the messages themselves. Systems commonly use such data structures and message formats in situations that require the electronic, structured, and computable exchange of important information, such as medical data.

However, it may be difficult or impossible to accommodate such large and complex structured message formats in environments and situations that lack the network infrastructure and device capabilities that would typically facilitate the use of such message structures and formats, such as the DIL environments described above. In such environments and situations, there are limits on the time, size, and/or amount of data that can be transmitted, received, and/or stored at any given time. Therefore, in such environments and situations, it may be advantageous to compress data and/or optimize data transmission to maximize the amount of information that can be transmitted and received in the least amount of time and using the least amount of resources.

Various embodiments are described herein that use algorithms and compression methods for transmitting structured and computable data that may, for example, facilitate data exchange in DIL environments. The disclosed systems and methods may also provide means for transmitting large amounts of structured data more efficiently. While some of the examples used herein may be described specifically in regard to the exchange and storage of medical information in DIL environments, one skilled in the art will recognize that various disclosed embodiments may be applicable to the exchange and storage of any type of data in any type of environment and may be used in any system that transmits, receives, and/or stores data. Various disclosed embodiments may further be used to compress and communicate any suitable structured dataset more efficiently.

In various embodiments, the system may generate a structured, compressed, and transmittable record that increases the amount of data carried by such a record using the methods and algorithms described herein to compress and encode structured data, such as medical data. In various embodiments, such data may be received, stored, and/or processed on a smart bandage and transmitted to other devices from a smart bandage as described herein, such as the smart bandage 300. In other various embodiments, such data may be received, stored, and/or processed on a computing device for transmittal to a smart bandage or other smart wearable device as described herein, such as the smart bandage 300. In particular embodiments, such data may be received, stored, and/or processed on a computing device after receipt from such a smart bandage/device.

Byte Level Representation of Coded, Computable Data Elements

In various embodiments, the system may employ a dynamic data model that may be updated and/or modified based on one or more needs of users and one or more issues being addressed by the system. Data models according to various embodiments may be used to structure or otherwise organize computable data (e.g., data that is to be transmitted and/or stored as structured, coded values). In particular embodiments, such computable data may include medical information represented using a predefined terminology set, such as, but not limited to, Logical Observation Identifiers Names and Codes (LOINC), Systematized Nomenclature of Medicine-Clinical Terms (SNOMED-CT), Current Procedural Terminology (CPT), and National Drug Code (NDC) codes. Such codes or terminology used in the data may describe any action, place, and/or entity that is applicable to a patient. For example, the system may use SNOMED-CT codes for heart rate, blood pressure, and oxygen saturation to identify each of these vital signs and indicate its respective value in a data structure that the system may transmit, receive, and/or store.

In various embodiments, the system may use a data model that captures, in one or more data tables, a set of data that may be transmitted. This data model may map the information that would be otherwise require a more complex and lengthier message for transmission to a single byte. The system may use the byte code mapping defined by this data model to encode information (e.g., vital signs, medical data, etc.) and compress the information into a much smaller number of bits of data for transmission, in some examples, into a single byte. In particular embodiments, the system may also, or instead, use a data model that maps information to a code that uses only a few (e.g., 2, 3, 4, 1-10, less than 100, etc.) bytes.

In various embodiments, the system may include a first system, a second system, and one or more intermediate systems, such as a smart bandage, that may have relatively reduced data storage capacity. The first system and the second system may be configured with the encoding tables so that each may be able to compress and decompress (e.g., encode and decode) data to determine the data's full, computable, and readable form. In particular embodiments, the first system may compress and/or encode healthcare data using an encoding table and transmit such data to an intermediate device such as a smart bandage that may store the compressed data. At a later time, the second system may retrieve the compressed data from the intermediate system and decompress and/or decode the data using the same encoding table to reveal the full, computable, and readable form of the data.

Data Structures

In various embodiments, the system may use a targeted layout to minimize the number of bytes needed for each type of data element that the system may encode and/or compress. In a particular embodiment, the system may stack one or more computed byte values derived using, for example, a data model or encoding table as described herein, in a particular order. The system may then transmit or otherwise write these stacked values to an output data stream and/or store them in a target device as compressed data. In particular examples, the output data stream of stacked values (the compressed data) may be transmitted to a smart bandage for storage and transport with a patient.

For example, the system may compress medical data such as vital signs using a structured layout for each vital sign, where an example layout may be represented by:

Vital Code,Unit of Measure,ObservedMeasurement, Timestamp

The system may eliminate the use of separators (e.g., byte-sized indicators) to indicate each of both the beginning and the end of each encoded value (e.g., vital code, unit of measure, etc.), thereby saving two bytes of space in a compressed record. In various embodiments, the system may insert a separator value between an indication of an observed measurement and an indication of a timestamp and/or at the end of a record to facilitate the recognition of these values (e.g., by this and/or other systems), rather than a separator value indicating the end of one of these pieces of data and then another separator indicating the beginning of the next piece of data. A separator byte value may be used to address variable length values and timestamps that may not be predictable. However, even with variable measurement or numeric values such as a timestamp, the system may convert these values to bit value representations that may be represented as bytes. By using bit-level values and corresponding byte representations, the system may eliminate the use of strings for numeric values (e.g., a string representing the characters associated with the numeric value) and compress numbers down significantly by indicating the numeric values in binary. For example, the system may represent the decimal value "1000" as the binary value "1111101000" in bits which can be stored in two bytes, rather than the four bytes that would be required to represent the decimal value "1000" as a string of the characters '1' '0' '0' '0'.

In various embodiments, the system may reserve one or more (e.g., four) byte codes to serve as markers to facilitate the recognition of separations between values. In a particular embodiment, the system may reserve a byte code for representing each of: (1) a separation of individual complete records; (2) a separation of values when the value is of variable length; (3) a separation of sections of data; and/or (4) a demarcation of an end of a complete data record. The system may also, or instead, use other byte values to indicate any other separation or demarcation.

Bit Packing and Optimizing Space

When compressing structured data, storage space may be wasted when the actual amount of data associated with a defined segment of data consumes less space than the allocated or allotted space for that segment in the structured layout of a record. In various embodiments, the system may reduce such wastage by analyzing each segment of data as it is compressed and comparing the space requirements for the actual data to be included in a segment against the allocated space assigned to that segment in the record. If the system determines that the amount of space needed for the actual data as encoded and compressed is less than the space allocated to that segment, the system may use the remaining, unused space for the next segment of data. In this way, the system may ensure that "blank" or empty space in the compressed record is not wasted, thereby reducing the overall storage space consumed by the record. The system may use one or more special byte code designators as described herein to indicate that an end of data segment or record has been reached (e.g., when the segment or record requires less space than normally used or allotted to it).

By employing these bit packing analysis techniques, some of the various disclosed embodiments may ensure that data is compressed sufficiently to fit within a target record size. For example, the system may compress medical data sufficiently to be stored on one or more small form factor devices, such as near-field communications (NFC) Tag 216 stickers and within Quick Response (QR) codes. NFC Tag 216 stickers have a physical storage limit of 888 bytes, while QR codes have a storage limit of approximately 2900 bytes with limited error correction. In such embodiments, packing data (e.g., as bytes) efficiently may help maximize the amount of information that can be transmitted within the space constraints of the device/sticker. In other embodiments, the system may compress medical data in order to optimize the use of data storage media on devices that have relatively larger storage capacity, such as a smart bandage.

Data Compression Prioritization

In various embodiments, the system may prioritize the compression of one or more specific data segments in determining how to utilize unused space in a data structure. The system may designate one or more particular data segments and/or structures as being higher priority when performing bit packing and/or compression. For example, when attempting to meet a maximum byte threshold that may be based on a target device's storage capacity or other criteria, the system may prioritize particular data segments and/or structures in determining an order in which to compress segments or structures.

For example, in a medical information messaging and data exchange scenario, the system may specify that one or more particular types of information are more important and should take precedence over other information when the total amount of data being processed (e.g., compressed, bit packed, etc.) exceeds data storage limitations of the target device following the processing. In a particular embodiment, the system may specify that medication administration events and vital observations collected for a patient have a higher priority than demographic information or general observation notes. By applying this prioritization, the system may rearrange the data within a record to be transmitted and/or stored, tailoring the compressed data set to the storage size of a recipient target device. In this way, the system may ensure that the most important information is stored on, and/or transmitted to, a recipient device by tailoring the compression of the data based on structure, data type, and importance. The system may ensure that the important data is stored and/or transmitted first, and if any data is ultimately unable to fit in the allotted space, the prioritization will ensure that the data left off is less important data.

Exemplary Algorithm for Structured and Configurable Data Compression/Decompression HL7 messages, such as FHIR, may transmit computable medical data on a patient using a structure such as the example shown below in Table 1 for a set of vital signs on a patient. As can be seen, this structure may be complex and may use multiple levels of nesting to establish a hierarchy of information to describe and transmit a patient's vital signs, such as respiratory rate, heart rate, blood pressure, and body temperature.

TABLE 1

Example HL7 Message Structure

```
{
  "resourceType": "Observation",
  "id": "vitals-panel",
  "meta": {
    "profile"; [
      "http://h17.org/fhir/StructureDefinition/vitalsigns"
    ]
  },
  "text": {
    "status": "generated",
    "div": "<div xmlns=\"http://www.w3.org/1999/xhtml\"><p><b>Generated Narrative with
Details</b></p><p><b>id</b>: vitals-panel</p><p><b>meta</b>: </p><p><b>status</b>:
final</p><p><b>category</b>: Vital Signs <span>(Details :
{http://terminology.h17.org/CodeSystem/observation-category code 'vital-signs' = 'Vital Signs',
given as 'Vital Signs'})</span></p><p><b>code</b>: Vital signs Panel <span>(Details : {LOINC code
'85353-1' = 'Vital signs, weight, height, head circumference, oxygen saturation &amp; BMI panel',
given as 'Vital signs, weight, height, head circumference, oxygen saturation and BMI
panel'})</span></p><p><b>subject</b>: <a>Patient/example</a></p><p><b>effective</b>:
02/07/1999</p><p><b>hasMember</b>: </p><ul><li><a>Respiratory Rate</a></li><li><a>Heart
Rate</a></li><li><a>Blood Pressure</a></li><li><a>Body Temperature</a></li></ul></div>"
  },
  "status": "final",
  "category": [
    {
      "coding": [
        {
          "system": "http://terminology.h17.org/CodeSystem/observation-category",
          "code": "vital-signs",
          "display": "Vital Signs"
        }
      ],
      "text": "Vital Signs"
    }
  ],
  "code": {
    "coding": [
      {
```

TABLE 1-continued

Example HL7 Message Structure

```
          "system": "http://loinc.org",
          "code": "85353-1",
          "display": "Vital signs, weight, height, head circumference, oxygen saturation and BMI
panel"
        }
      ],
      "text": "Vital signs Panel"
  },
  'subject":
      "reference": "Patient/example"
  },
  "effectiveDateTime": "1999-07-02",
  "hasMember": [
      {
        "reference": "Ohservation/respiratory-rate",
        "display": "Respiratory Rate"
      },
      {
        "reference": "Observation/heart-rate",
        "display": "Heart Rate"
      },
      {
        "reference": "Observation/blood-pressure",
        "display": "Blood Pressure"
      },
      {
        "reference": "Observation/body-temperature",
        "display": "Body Temperature"
      }
  ]
}
```

Values used in a message structure such as that shown in Table 1 may be encoded as shown in the example provided in Table 2 below. In this example, a single body temperature observation of 36.5 C is represented using coded terminology sets to define that the measure is body temperature (LOINC Code 8310-5) and the unit of measure of the temperature value is in Celsius. In addition, the time of the observation is encoded.

TABLE 2

Example Value Encoding

```
{
  "resourceType": "Observation",
  "id"; "body-temperature",
  "meta": {
    "profile": [
      "http://h17.org/fhir/StructureDefinition/vitalsigns"
    ]
  },
  "text": {
    "status": "generated",
    "div": "<div xmlns=\"http://www.w3.org/1999/xhtml\"><p><b>Generated Narrative with
Details</b></p><p><b>id</b>: body-temperature</p><p><b>meta</b>: </p><p><b>status</b>:
final</p><p><b>category</b>: Vital Signs <span>(Details :
{http://terminology.h17.org/CodeSystem/observation-category code 'vital-signs' = 'Vital Signs',
given as 'Vital Signs'})</span></p><p><b>code</b>: Body temperature <span>(Detalls : {LOINC code
'8310-5' = 'Body temperature', given as 'Body temperature'})</span></p><p><b>subject</b>:
<a>Patient/example</a></p><p><b>effective</b>: 02/07/1999</p><p><b>value</b>: 36.5 C<span> (Details:
UCUM code Cel = 'Cel')</span></p></div>"
  },
  "status": "final",
  "category": [
    {
      "coding": [
        {
          "system": "http://terminology.h17.org/CodeSystem/observation-category",
          "code": "vital-signs",
          "display": "Vital Signs"
        }
      ],
      "text": "Vital Signs"
    }
  ]
  "code": {
    "coding": [
```

TABLE 2-continued

Example Value Encoding

```
      {
        "system": "http://loinc.org",
        "code": "8310-5"
        "display": "Body temperature"
      }
    ],
    "text": "Body temperature"
  },
  "subject": {
    "reference": "Patient/example"
  },
  "effectiveDateTime": "1999-07-02",
  "valueQuantity": {
    "value": 36.5,
    "unit': "C",
    "system": "http://unitsofmeasure.org",
    "code": "Cel"
  }
}
```

In various embodiments, the system may reduce the repetitiveness and nested structure of a record storing such information, as well as reduce the size of representations of coded values. Rather than representing a coded value using a lengthy code (e.g., the LOINC value 8310-5 seen in the tables above), the system may perform byte level encoding using the following structure and representation of that value within a record to compress the data, as shown in the example of Table 3.

TABLE 3

Example Byte Level Value Encoding

```
"code": {
  "coding": [
    {
      "system": "http://loinc:org",
      "code": "8310-5",
      "display": "Body temperature"
    }
  ],
  "text": "Body temperature"
},
```

The system may use one or more look-up tables for encoding. Such look-up tables may be updated, amended, and expanded as needed. Look-up tables may be domain-specific (e.g., specific to lab values, vital signs, medications, procedures, units of measure, etc.) and may contain the information such as coding system, code value, and display. Look-up tables may include one or more "byte values" that may each be a special character that is unique to the code the system is encoding and to the associated domain, as shown in the following example look-up of Table 4.

TABLE 4

Example Encoding Look-up Table

| Code System | Code Value | Display Text | Encoding Byte |
|---|---|---|---|
| http://loinc.org | 8310-5 | Body Temperature | 126 (~) |

By using a table for vital observations as shown in Table 4 above, the system may encode a body temperature code value using an encoding byte value of 126. Thus, the system may represent a structural encoded body temperature as a single byte of data. In this example, the value for the body temperature may be represented in binary at the $126^{th}$ byte. Because the system is using an encoding table specific to vitals and a byte, it will not be limited to only 256 bytes because the system may use both context (vital) and an encoding byte (126) to enable the encoding of 256 unique vital entries according to the table and for use in the disclosed embodiments. If even more values are needed, the system may use a secondary encoding byte that would provide, for example, 256×256 (65,536) encoding byte pair combinations for use in representing values for any domain type.

By using an encoding byte, the system may reduce the size of a substructure such as that shown in the example for body temperature, for example, from 195 bytes to one byte. By using this approach for mapping, compressing, and ultimately encoding data for all of various domains of data, the system may achieve the same or better compression in representing each of the coded values for a variety of types of data as a single byte. The system may use a known order of bytes in the structure of a message to ensure that the context of each segment of such a message is known and thereby enable the use of look-up tables to determine the information represented by the segments of the message. For example, the system may determine the value for the body temperature in binary and store and/or transmit that binary value as the $126^{th}$ byte of the record generated using the look up table of Table 4. That body temperature value is associated with the LOINC code value 8310-5 and the display text "Body Temperature." By using a similar look up table at a receiving device, the receiving device can readily determine the $126^{th}$ byte of the received record is a binary representation of body temperature associated with the LOINC code value 8310-5 and the display text "Body Temperature."

In various embodiments, the system may use a data structure similar to that of HL7 2.x formats for encapsulating patient records and to take advantage of the disclosed encoding and context-aware compression methods. Note that the example data structures and record configurations described herein are meant to be representative and other structures and implementations may be used without departing from the scope of this disclosure. The following example shown in Table 5 is an example of a generic data structure according to various embodiments that does not necessarily take into account any specific target but rather illustrates a general approach to structuring data at the byte level to achieve the compression goals described.

In a particular embodiment, the system structures a patient record based on a patient that has one or more encounters (e.g., visits or interactions with a care provider). In this example, a Tactical Combat Casualty Care (TCCC) card may be used to record traumatic injuries incurred in the battlefield. Each encounter may result in numerous patient vital observations, medications dispensed, procedures performed, and injuries noted that the system may record on the TCCC card. In the operational medicine environment, each such encounter record may represent a role of care from when a patient is wounded and first treated in a DIL environment, through transport where DIL conditions may or may not be present, and ultimately back to a hospital where DIL conditions are no longer be applicable. Table 5 illustrates the layout of an example of such a record.

TABLE 5

| Example Encounter Record |
|---|
| \| - (1-1) Demographics - First, Last, Gender, Rank, Branch, IDNum |
| \| - (1 . . . N) Encounter - Timestamp |
| \| - (1 . . . N) Vital |
| \| - Vital Code, Vital Unit Code, Vital Measurement, Timestamp |
| \| - (1 . . . N) Medication |
| \| - Medication Code, Dispensed Value, Dispensed Unit, TimeStamp Offset |
| \| - (1 . . . N) Injury |
| \| - Injury Code, Location Code, TimeStamp Offset |
| \| - (1 . . . N) Procedure |
| \| - Procedure Code, Location Code, Timestamp Offset |

In the example record of Table 5, the record may include a structure for patient demographics followed by a structure for a particular encounter that occupies a predefined number of bytes (e.g., 1-N bytes). Within the encounter structure, a first particular set of bytes may be a substructure of a particular number of bytes that represents vital signs, where the order of the bytes indicates the particular vital sign data (e.g., the first byte of the substructure is the vital code, the second byte of the substructure is the vital unit code, the third byte of the substructure is the vital measurement, etc.). After the vital signs substructure, the next substructure may be a particular set of bytes that represents medications, where the order of the bytes indicates the particular medication data (e.g., the first byte of the substructure is the medication code, the second byte of the substructure is the dispensed value, the third byte of the substructure is the dispensed unit, etc.). By using a look up table as described above, the information in a record, such as the exemplary record of Table 5, may be encoded and stored in a minimal amount of space and transmitted using a minimal amount of resources.

Structured and Configurable Data Compression/Encoding Module

Figure 5:
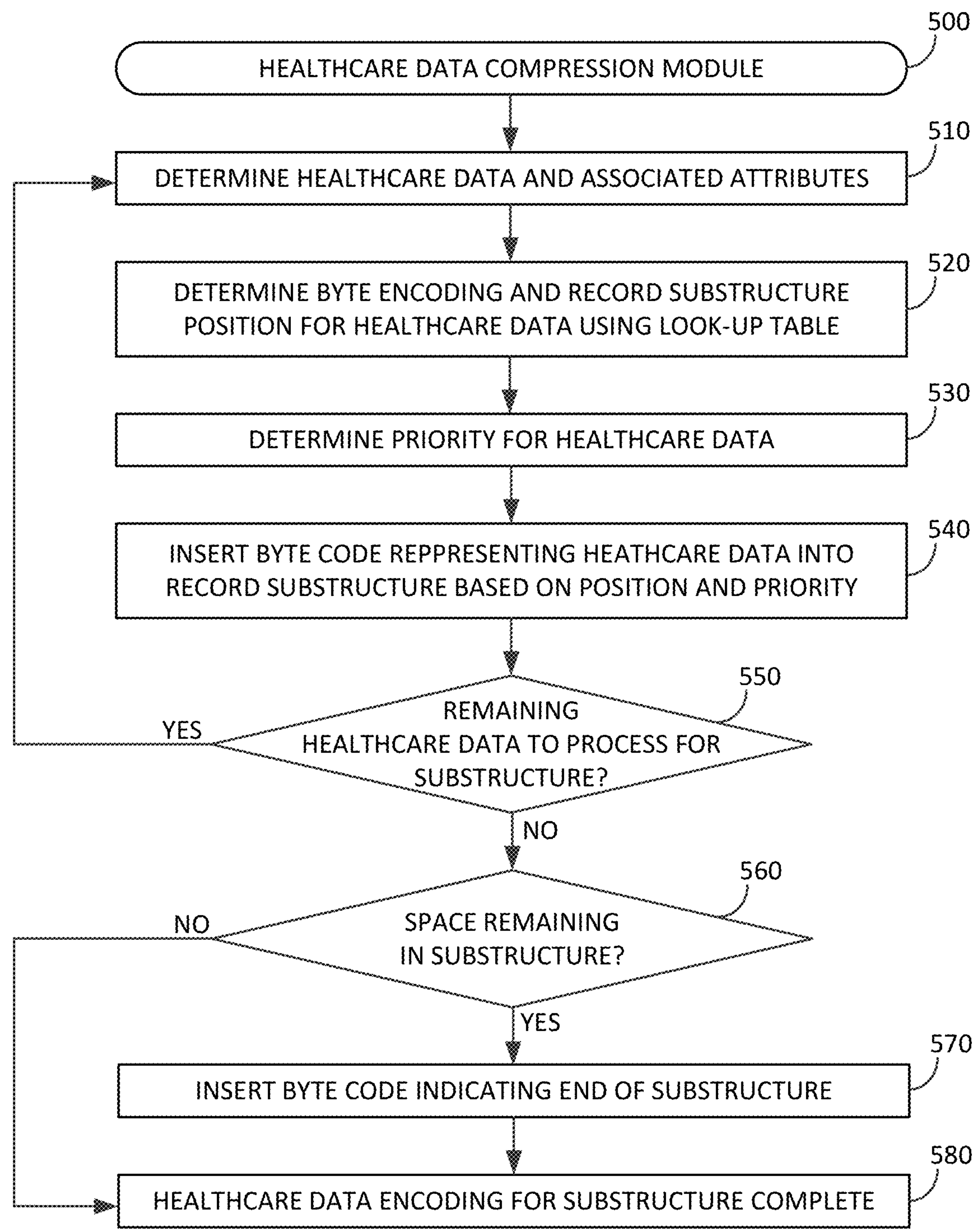
FIG. 5 is a flow chart showing an example of a process performed by a Healthcare Data Compression Module.

FIG. 5 illustrates an example process that may be performed by a Healthcare Data Compression Module 500 according to the disclosed embodiments. In executing the Healthcare Data Compression Module 500, the system begins at Step 510 where a particular piece of healthcare data may be determined, for example, as entered by a healthcare provider on a mobile device as health measurements are taken on a patient; received as a portion of a transmission of healthcare data, etc. The system may determine attributes of the particular piece of healthcare data at Step 510 that, for example, that may be used to determine the byte-level encoding for the particular piece of healthcare data. For example, the system may determine the numeric value (e.g., represented by characters in s string) of a body temperature along with the associated attributes of the LOINC code value 8310-5 and the display text "Body Temperature."

At Step 520, the system may determine the byte encoding for the particular piece of healthcare data using a look-up table. In a particular embodiment, using the particular piece of healthcare data and, in some embodiments, one or more associated attributes, the system may determine the particular position of the byte to be used to represent the particular piece of healthcare data using a look-up table such as that shown in Table 4. The system may also determine a manner and/or type of encoding (e.g., as a binary value representing the particular piece of healthcare data, as a special byte code designator, etc.). In this particular example, the system may determine that, for the particular piece of healthcare data that is a body temperature with the LOINC code value 8310-5, the position of a byte within the vital signs substructure representing this body temperature in a the $126^{th}$ byte. The look-up table may also specify that the body temperature is to be stored as a binary value representing the body temperature in the $126^{th}$ byte of the appropriate substructure. The look-up table may also, or instead, include any other information that the system may use to map one or more bytes to a piece of healthcare data. Such mapping may take any suitable form, including, by not limited to a position of a byte in a structure, substructure, and/or record associated with a particular type of healthcare data. The look-up table may also, or instead, include any other information that the system may use to specify how the piece of healthcare data is to be encoded in one or more bytes (e.g., an indicator instructing the system to encode the piece of healthcare data as a binary value representing the particular piece of healthcare data, as a special byte code designator, etc.).

At Step 530, the system may determine a priority of the particular piece of healthcare data. As described above, in particular embodiments, where there may be storage limitations to the amount of data that can be stored or transmitted, the system may determine that some information is more important than other information, and may be configured to insert information of greater importance into a stream of encoded information earlier than information that is of lesser importance.

At Step 540, the system may insert (e.g., store, transmit, etc.) the determined byte code for the particular piece of healthcare data into the structure, substructure, and/or record currently being processed (e.g., encoded, compressed) based on the position determined from the look-up table and/or the priority associated with the particular piece of healthcare data.

At Step 550, the system may determine whether there remains any further healthcare data to be processed (compressed, encoded, transmitted, stored, etc.). If there is remaining healthcare data to be processed, the system may return to Step 510 to resume such processing.

If the system determines, at Step 550, that there is no further healthcare data to process, then at Step 560 the system may determine if there is unused space remaining in the sequence of encoded bytes allotted to the sections of healthcare data associated with the healthcare data currently being processed (e.g., remaining space in the associated structure, substructure, record, etc.). If there is remaining space in the particular sequence of encoded bytes associated with the healthcare data being processed, at Step 570 the system may insert a special byte code indicating that the particular sequence of encoded bytes is complete, thereby allowing the system to begin encoding the next sequence of encoded bytes directly after the special byte code, using space that would otherwise have gone unused. This particular special byte code may also serve as indicator to the device receiving or reading the particular sequence of encoded bytes that this particular sequence of encoded bytes is complete.

At Step 580, after processing the particular healthcare data (and, in particular embodiments, after inserting a special byte code indicating the end of this particular sequence of encoded bytes), the processing of the healthcare data is complete. The system may then process other healthcare data, store the encoded healthcare data, transmit the encoded healthcare data, or perform any other suitable functions using the healthcare data.

Structured and Configurable Data Decompression/Decoding Module

Figure 6:
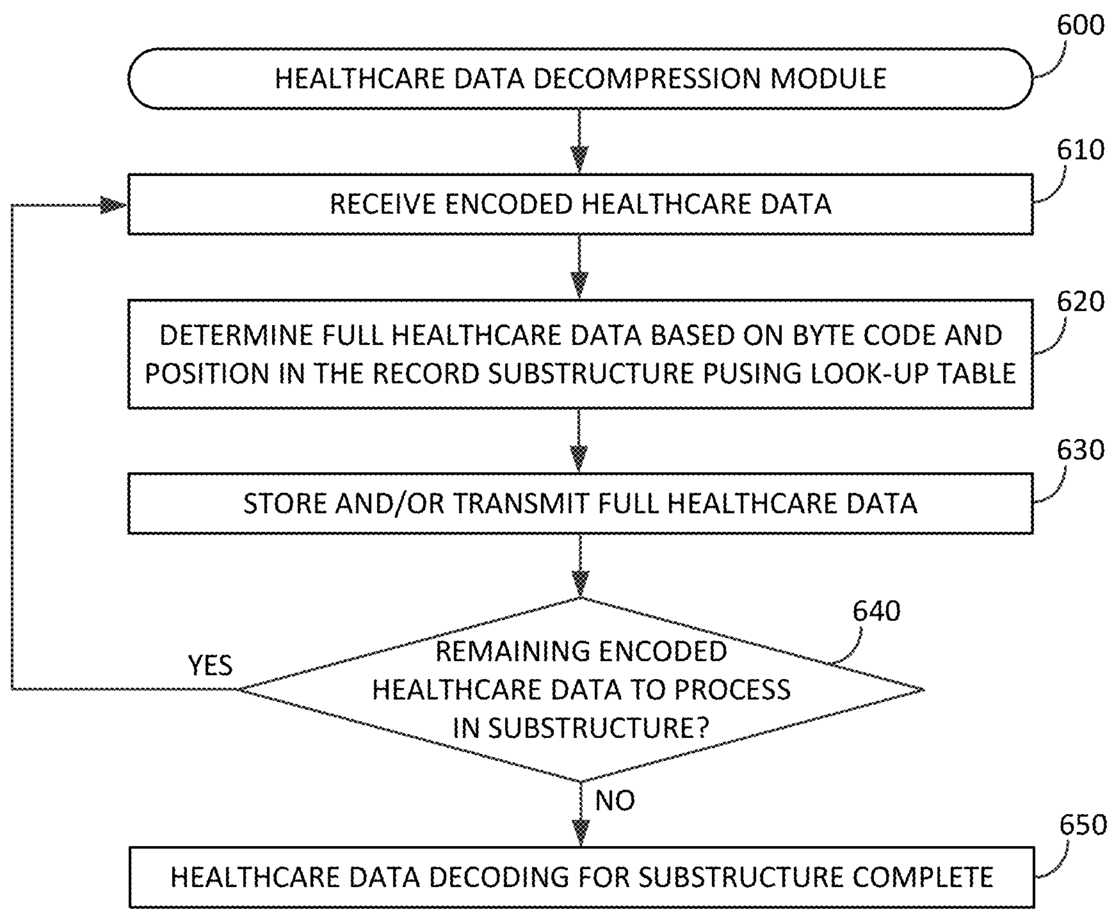
FIG. 6 is a flow chart showing an example of a process performed by a Healthcare Data Decompression Module.

FIG. 6 illustrates an example process that may be performed by a Healthcare Data Decompression Module 600 according to the disclosed embodiments. In executing the Healthcare Data Decompression Module 600, the system begins at Step 610 by receiving encoded healthcare data, such as a sequence of encoded bytes associated with, for example, a particular type of healthcare data (e.g., a structure, substructure, record, etc.). The system may receive a full sequence of healthcare data encoded bytes for processing or may receive and process individual encoded bytes.

At Step 620, the system may determine the full health data for a particular encoded byte using a look-up table, such as look-up Table 4 above. In various embodiments, the system may use the look-up table to determine attributes of the particular piece of healthcare data associated with the particular encoded byte by locating the entry in the encoding table associated with the position of the particular encoded byte in its associated particular sequence of encoded bytes. The system may then use this look-up table entry to determine the attributes of the particular piece of healthcare data associated with the particular encoded byte as well as any information that may be used to return the particular encoded byte to its decoded form. For example, the entry associated with the particular encoded byte in the look-up table may indicate that the numeric value contained in the particular encoded byte as a binary value should be represented as a string of characters when decoded. In the particular example illustrated in Table 4, the system may determine that the particular encoded byte in the $126^{th}$ position of this particular sequence of encoded bytes is associated with a particular piece of healthcare data that is a body temperature having the LOINC code value 8310-5. The look-up table may also specify that the body temperature, as decoded, is to be stored as a numeric value represented by a string of characters. The look-up table may also, or instead, include any other information that the system may use to map one or more encoded bytes to a particular full (e.g., decoded) healthcare record.

At Step 630, the system may store, transmit, and/or perform any other processing on the decoded particular piece of healthcare data derived from the particular encoded byte. At Step 640, the system may determine if there are any remaining encoded bytes in this particular sequence of encoded bytes to be processed. If so, the system may return to Step 610 to continue processing (e.g., decoding, decompressing) the encoded bytes in this particular sequence of encoded bytes. If there are not further encoded bytes in this particular sequence of encoded bytes, at Step 650 the processing of this particular sequence of encoded bytes may be complete.

As one skilled in the art will recognize, the examples described herein in regard to the specific use, compression, encoding, processing, and transmittal of medical information, including the use of value encoding tables, structured records, bit packing, and prioritization of data, may be applied to any structured data set across any industry type where information exchange may be performed. Examples of such implementations according to the disclosed embodiments include, but are not limited to, transmittal of hardware data, service records, capturing and tracking audit log information, machine maintenance records, real-time telemetry data, etc. The disclosed embodiments are not limited to any particular device or transmission method.

CONCLUSION

Although embodiments above are described in reference to various data storage and exchange systems, it should be understood that various aspects of the system described above may be applicable to other types of systems, in general.

While this specification contains many specific embodiment details, these should not be construed as limitations on the scope of any invention or of what may be claimed, but rather as descriptions of features that may be specific to particular embodiments of particular inventions. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations may be described in a particular order, this should not be understood as requiring that such operations be performed in the particular order described or in sequential order, or that all described operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

What is claimed is:

1. A user-affixable device configured to perform data processing of healthcare data, the user-affixable device comprising:

a bandage comprising an adhesive portion, an absorbent portion, and a water-resistant flexible encapsulation portion, wherein the water-resistant flexible encapsulation portion is configured to encapsulate a plurality of electronic components, and wherein the plurality of electronic components comprises:

a microprocessor;

data storage media communicatively connected to the microprocessor;

a near-field communications (NFC) processor communicatively connected to the microprocessor;

an NFC antenna communicatively connected to the NFC processor, wherein the NFC processor is configured to:

at least partially in response to receiving an NFC signal from an NFC initiator device via the NFC antenna, establish an NFC field with the NFC initiator device;

at least partially in response to establishing the NFC field with the NFC initiator device, transmit an activation signal to the microprocessor;

detect a breaking of the NFC field; and at least partially in response to detecting the breaking of the NFC field, transmit a deactivation signal to the microprocessor;

a power supply configured to supply power to the microprocessor;

a Bluetooth processor communicatively connected to the microprocessor; and a Bluetooth antenna communicatively connected to the Bluetooth processor;

wherein the microprocessor is configured to:

at least partially in response to receiving the activation signal from the NFC processor, provide power to the data storage media and the Bluetooth processor;

at least partially in response to receiving the deactivation signal from the NFC processor, cease providing power to the data storage media and the Bluetooth processor; and wherein the Bluetooth processor is configured to, at least partially in response to receiving power from the microprocessor, establish a Bluetooth communications session with a wireless communications device.

2. The user-affixable device of claim 1, wherein the Bluetooth processor is further configured to:

detect a termination of the Bluetooth communications session with the wireless communications device; and at least partially in response to detecting the termination of the Bluetooth communications session with the wireless communications device, transmit a deactivation signal to the microprocessor.

3. The user-affixable device of claim 2, wherein the microprocessor is further configured to:

at least partially in response to receiving the deactivation signal from the Bluetooth processor, cease providing power to the data storage media and the Bluetooth processor.

4. The user-affixable device of claim 1, wherein the wireless communications device is a computing device distinct from the NFC initiator device.

5. The user-affixable device of claim 1, wherein the Bluetooth processor is configured to, at least partially in response to receiving power from the microprocessor, transmit a message to the NFC initiator device indicating that the user-affixable device has Bluetooth capabilities.

6. The user-affixable device of claim 5, wherein the Bluetooth processor is configured to establish the Bluetooth communications session with the NFC initiator device via the Bluetooth antenna.

7. The user-affixable device of claim 1, wherein the Bluetooth processor is configured to:

receive healthcare data via the Bluetooth antenna; and transmit the healthcare data to the microprocessor for storage at the data storage media.

8. A data processing system for processing healthcare data, the data processing system comprising:

a housing;

a moisture-resistant encapsulation portion configured within the housing;

a microprocessor configured within the moisture-resistant encapsulation portion;

data storage media configured within the moisture-resistant encapsulation portion and communicatively connected to the microprocessor;

a near-field communications (NFC) processor configured within the moisture-resistant encapsulation portion and communicatively connected to the microprocessor;

an NFC antenna configured within the moisture-resistant encapsulation portion and communicatively connected to the NFC processor, wherein the NFC processor is configured to:

at least partially in response to receiving an NFC signal from an NFC initiator device via the NFC antenna, establish an NFC field with the NFC initiator device; and at least partially in response to establishing the NFC field with the NFC initiator device; transmit an activation signal to the microprocessor;

a power supply configured within the moisture-resistant encapsulation portion and configured to supply power to the microprocessor;

a wireless communications processor configured within the moisture-resistant encapsulation portion and communicatively connected to the microprocessor; and one or more wireless communications antennas configured within the moisture-resistant encapsulation portion and communicatively connected to the wireless communications processor;

wherein the microprocessor is configured to:

at least partially in response to receiving the activation signal from the NFC processor, provide power to the data storage media and the wireless communications processor;

receive a request for healthcare data from the wireless communications processor;

at least partially in response to receiving the request for healthcare data from the wireless communications processor, retrieve requested healthcare data from the data storage media; and transmit the requested healthcare data to the wireless communications processor; and wherein the wireless communications processor is configured to:

at least partially in response to receiving power from the microprocessor, establish a wireless communications session with a wireless communications device using the one or more wireless communications antennas;

receive the request for the healthcare data from the wireless communications device via the wireless communications session;

transmit the request for the healthcare data to the microprocessor;

receive the requested healthcare data from the microprocessor; and transmit the requested healthcare data to the wireless communications device via the wireless communications session using the one or more wireless communications antennas.

9. The data processing system of claim 8, wherein:

the wireless communications processor is a Wi-Fi processor;

the one or more wireless communications antennas are one or more Wi-Fi antennas; and the wireless communications session is a Wi-Fi communications session.

10. The data processing system of claim 8, wherein the requested healthcare data comprises a sequence of encoded bytes.

11. The data processing system of claim 8, wherein:

the NFC processor is further configured to detect a breaking of the NFC field; and at least partially in response to detecting the breaking of the NFC field, the NFC processor is further configured to transmit a deactivation signal to the microprocessor.

12. The data processing system of claim 11, wherein:

at least partially in response to receiving the deactivation signal from the NFC processor, the microprocessor is configured to transmit an instruction to the wireless communications processor to terminate the wireless communications session with the wireless communications device.

13. The data processing system of claim 8, wherein the housing is a band suitable for attachment about a human arm or a human leg.

14. The data processing system of claim 8, wherein the housing is a bandage suitable for attachment to human skin.

15. A method of operating a healthcare data processing system, the method comprising:

establishing, by a near-field communications (NFC) processor via an NFC antenna, an NFC field with an NFC initiator device, wherein the NFC processor and the NFC antenna are encapsulated in a moisture-resistant bandage housing;

transmitting an activation signal from the NFC processor to a microprocessor, wherein the microprocessor is encapsulated in the moisture-resistant bandage housing;

at least partially in response to receiving the activation signal from the NFC processor, providing power, by a battery via the microprocessor, to a Bluetooth processor and data storage media, wherein the battery, the Bluetooth processor, and the data storage media are encapsulated in the moisture-resistant bandage housing;

at least partially in response to receiving power from the battery via the microprocessor, establishing, by the Bluetooth processor via one or more Bluetooth antennas, a Bluetooth communications session with the NFC initiator device; wherein the one or more Bluetooth antennas are encapsulated in the moisture-resistant bandage housing;

exchanging data, by the Bluetooth processor using the one or more Bluetooth antennas, via the Bluetooth communications session with the NFC initiator device;

detecting, at the Bluetooth processor via the one or more Bluetooth antennas, a termination of the Bluetooth communications session with the NFC initiator device;

at least partially in response to detecting the termination of the Bluetooth communications session with the NFC initiator device, transmitting, from the Bluetooth processor, a deactivation signal to the microprocessor; and at least partially in response to receiving the deactivation signal from the Bluetooth processor, ceasing, by the microprocessor, providing power from the battery to the Bluetooth processor and the data storage media.

16. The method of claim 15, further comprising:

establishing, by the Bluetooth processor using the one or more Bluetooth antennas, one or more Bluetooth sessions with one or more respective health data sensors configured on a human user;

receiving, via the one or more Bluetooth sessions with the one or more respective health data sensors, by the Bluetooth processor using the one or more Bluetooth antennas, health measurement data;

transmitting, from the Bluetooth processor to the microprocessor, the health measurement data;

receiving, at the microprocessor from the Bluetooth processor, the health measurement data; and storing, by the microprocessor, the health measurement data in the data storage media.

17. The method of claim 16, wherein one or more of the one or more health data sensors is a sensor selected from a group consisting of:

(a) a heart rate sensor;

(b) a body temperature sensor;

(c) a sweat sensor;

(d) a biosensor; and (e) an environmental sensor.

18. The method of claim 16, wherein exchanging data via the Bluetooth communications session with the NFC initiator device comprises:

retrieving, by the microprocessor, a subset of the health measurement data from the data storage media;

transmitting the subset of the health measurement data from the microprocessor to the Bluetooth processor;

receiving the subset of the health measurement data from the microprocessor at the Bluetooth processor; and transmitting the subset of the health measurement data from the Bluetooth processor to the NFC initiator device via the Bluetooth communications session with the NFC initiator using the one or more Bluetooth antennas.

* * * * *

UNITED STATES PATENT AND TRADEMARK OFFICE

CERTIFICATE OF CORRECTION

PATENT NO. : 10,786,395 B1
APPLICATION NO. : 16/882837
DATED : September 29, 2020
INVENTOR(S) : Joshua Michael Temkin et al.

It is certified that error appears in the above-identified patent and that said Letters Patent is hereby corrected as shown below:

In the Specification

In Column 1, after Line 19, please insert the following:
--GOVERNMENT LICENSE RIGHTS
This invention was made with government support under Contract No. W81XWH20C0103 awarded by Defense Health Agency / USA Med Research Acq Activity. The government has certain rights in the invention.--

Signed and Sealed this
Seventeenth Day of May, 2022

Katherine Kelly Vidal

Katherine Kelly Vidal
*Director of the United States Patent and Trademark Office*